(12) United States Patent
O'Shaughnessy et al.

(10) Patent No.: US 11,393,679 B2
(45) Date of Patent: Jul. 19, 2022

(54) METHODS FOR PLASMA DEPOSITING POLYMERS COMPRISING CYCLIC SILOXANES AND RELATED COMPOSITIONS AND ARTICLES

(71) Applicant: GVD Corporation, Cambridge, MA (US)

(72) Inventors: W. Shannan O'Shaughnessy, Cambridge, MA (US); Scott W. Morrison, Cambridge, MA (US); R. Austin Nowak, Cambridge, MA (US)

(73) Assignee: GVD CORPORATION, Cambridge, MA (US)

( * ) Notice: Subject to any disclaimer, the term of this patent is extended or adjusted under 35 U.S.C. 154(b) by 183 days.

(21) Appl. No.: 16/219,514

(22) Filed: Dec. 13, 2018

(65) Prior Publication Data

US 2019/0122884 A1    Apr. 25, 2019

Related U.S. Application Data

(63) Continuation-in-part of application No. PCT/US2017/037291, filed on Jun. 13, 2017.

(Continued)

(51) Int. Cl.
*B05D 1/00* (2006.01)
*C23C 16/40* (2006.01)
(Continued)

(52) U.S. Cl.
CPC .......... *H01L 21/02274* (2013.01); *A61N 1/00* (2013.01); *B05D 1/62* (2013.01); *C08G 77/045* (2013.01); *C08J 5/18* (2013.01); *C08K 5/14* (2013.01); *C23C 16/401* (2013.01); *C23C 16/50* (2013.01); *C23C 16/505* (2013.01);
(Continued)

(58) Field of Classification Search
None
See application file for complete search history.

(56) References Cited

U.S. PATENT DOCUMENTS 3,010,009 A    11/1961 Ducati
3,149,222 A     9/1964 Giannini
(Continued)

FOREIGN PATENT DOCUMENTS

CA    2338538    2/2000
EP    1948851    11/2012
(Continued)

OTHER PUBLICATIONS

O'Shaughnessy. Biomacromolecules 2007, 8, 2564-2570 (Year: 2007).*

(Continued)

*Primary Examiner* — Jose I Hernandez-Kenney
(74) *Attorney, Agent, or Firm* — Pabst Patent Group LLP

(57) ABSTRACT

Methods for plasma depositing polymers comprising cyclic siloxanes and related articles and compositions are generally provided. In some embodiments, the methods comprise flowing a precursor gas in proximity to a substrate within a PECVD reactor, wherein the precursor gas comprises an initiator and at least one monomer comprising a cyclic siloxane and at least two vinyl groups, and depositing a polymer formed from the at least one monomer on the substrate.

19 Claims, 6 Drawing Sheets

Related U.S. Application Data

(60) Provisional application No. 62/349,593, filed on Jun. 13, 2016.

(51) Int. Cl.

| | |
|---|---|
| *C23C 16/505* | (2006.01) |
| *H01L 21/02* | (2006.01) |
| *A61N 1/00* | (2006.01) |
| *C23C 16/50* | (2006.01) |
| *C08G 77/04* | (2006.01) |
| *C08J 5/18* | (2006.01) |
| *C08K 5/14* | (2006.01) |

(52) U.S. Cl.
CPC .. *H01L 21/02118* (2013.01); *H01L 21/02126* (2013.01); *H01L 21/02216* (2013.01); *B05D 2518/10* (2013.01); *C08J 2383/07* (2013.01); *C23C 2222/20* (2013.01)

(56) References Cited

U.S. PATENT DOCUMENTS

| | | | |
|---|---|---|---|
| 4,225,647 A | 9/1980 | Parent | |
| 4,533,575 A | 8/1985 | Melancon | |
| 4,869,922 A | 9/1989 | DAgostino | |
| 4,948,485 A | 8/1990 | Wallsten | |
| 5,233,153 A | 8/1993 | Coats | |
| 5,304,255 A * | 4/1994 | Li | C23C 16/505 |
| | | | 136/257 |
| 5,888,591 A | 3/1999 | Gleason | |
| 5,989,998 A | 11/1999 | Sugahara | |
| 5,990,013 A | 11/1999 | Berenguer | |
| 6,045,904 A | 4/2000 | Torikoshi | |
| 6,054,379 A | 4/2000 | Yau | |
| 6,110,544 A | 8/2000 | Yang | |
| 6,153,269 A | 11/2000 | Gleason | |
| 6,156,435 A | 12/2000 | Gleason | |
| 6,203,898 B1 | 3/2001 | Kohler | |
| 6,268,695 B1 | 7/2001 | Affinito | |
| 6,348,237 B2 | 2/2002 | Kohler | |
| 6,372,283 B1 | 4/2002 | Shim | |
| 6,432,494 B1 | 8/2002 | Yang | |
| 6,436,481 B1 | 8/2002 | Chabrecek | |
| 6,497,598 B2 | 12/2002 | Affinito | |
| 6,522,067 B1 | 2/2003 | Graff | |
| 6,548,912 B1 | 4/2003 | Graff | |
| 6,570,325 B2 | 5/2003 | Graff | |
| 6,572,923 B2 | 6/2003 | Ma | |
| 6,573,196 B1 | 6/2003 | Gaillard | |
| 6,573,652 B1 | 6/2003 | Graff | |
| 6,583,048 B1 | 6/2003 | Vincent | |
| 6,614,096 B2 | 9/2003 | Kojima | |
| 6,623,861 B2 | 9/2003 | Martin | |
| 6,649,222 B1 | 11/2003 | D Agostino | |
| 6,733,830 B2 | 5/2004 | Todd | |
| 6,803,660 B1 | 10/2004 | Gates | |
| 6,866,901 B2 | 3/2005 | Burrows | |
| 6,887,578 B2 | 5/2005 | Gleason | |
| 6,890,869 B2 | 5/2005 | Chung | |
| 6,923,702 B2 | 8/2005 | Graff | |
| 6,929,982 B2 | 8/2005 | Gates | |
| 6,936,551 B2 | 8/2005 | Moghadam | |
| 6,939,576 B2 | 9/2005 | Deshpande | |
| 6,962,671 B2 | 11/2005 | Martin | |
| 7,056,584 B2 | 6/2006 | Iacovangelo | |
| 7,074,690 B1 | 7/2006 | Gauri | |
| 7,081,673 B2 | 7/2006 | Hedrick | |
| 7,160,625 B2 | 1/2007 | Hara | |
| 7,198,832 B2 | 4/2007 | Burrows | |
| 7,256,146 B2 | 8/2007 | Cohen | |
| 7,282,238 B2 | 10/2007 | Shanmugham | |
| 7,396,758 B2 | 7/2008 | Huang | |
| 7,413,775 B2 | 8/2008 | Hara | |
| 7,459,404 B2 | 12/2008 | Li | |
| 7,470,597 B2 | 12/2008 | Hedrick | |
| 7,491,658 B2 | 2/2009 | Nguyen | |
| 7,514,151 B2 | 4/2009 | Shiota | |
| 7,521,318 B2 | 4/2009 | Ueno | |
| 7,524,735 B1 | 4/2009 | Gauri | |
| RE40,787 E | 6/2009 | Martin | |
| 7,557,369 B2 | 7/2009 | Humbs | |
| 7,582,555 B1 | 9/2009 | Lang | |
| 7,595,370 B2 | 9/2009 | Plehiers | |
| 7,727,601 B2 | 6/2010 | Burrows | |
| 7,736,634 B2 | 6/2010 | Plehiers | |
| 7,833,612 B2 | 11/2010 | Uhlig | |
| 7,888,233 B1 | 2/2011 | Gauri | |
| 7,901,832 B2 | 3/2011 | Trabold | |
| 7,915,139 B1 | 3/2011 | Lang | |
| 7,935,425 B2 | 5/2011 | Hara | |
| 7,951,705 B2 | 5/2011 | Hedrick | |
| 7,968,154 B2 | 6/2011 | Ward | |
| 7,968,471 B2 | 6/2011 | Harada | |
| 8,029,872 B2 | 10/2011 | Ward | |
| 8,057,813 B2 | 11/2011 | Toner | |
| 8,097,932 B2 | 1/2012 | Nguyen | |
| 8,106,385 B2 | 1/2012 | Ryuzaki | |
| 8,114,465 B2 | 2/2012 | Cahalan | |
| 8,313,812 B2 | 11/2012 | Coak | |
| 8,324,285 B2 | 12/2012 | Nicholas | |
| 8,343,567 B2 | 1/2013 | Cahalan | |
| 8,356,425 B2 | 1/2013 | Polegato Moretti | |
| 8,426,322 B2 | 4/2013 | Yamamoto | |
| 8,455,104 B2 | 6/2013 | Vissing | |
| 8,481,403 B1 | 7/2013 | Gauri | |
| 8,507,508 B2 | 8/2013 | Palle | |
| 8,536,629 B2 | 9/2013 | Tada | |
| 8,580,697 B1 | 11/2013 | Lang | |
| 8,618,420 B2 | 12/2013 | Humphries | |
| 8,809,161 B2 | 8/2014 | Gauri | |
| 8,900,663 B2 | 12/2014 | Handy | |
| 8,906,282 B2 | 12/2014 | Chan | |
| 8,945,478 B2 | 2/2015 | Coulson | |
| 8,955,217 B2 | 2/2015 | Burrows | |
| 8,995,146 B2 | 3/2015 | Brooks | |
| 8,997,378 B2 | 4/2015 | Polegato Moretti | |
| 9,006,355 B1 | 4/2015 | Fish | |
| 9,055,700 B2 | 6/2015 | Humphries | |
| 9,056,332 B2 | 6/2015 | Badyal | |
| 9,212,420 B2 | 12/2015 | Lee | |
| 2003/0228473 A1 | 12/2003 | Benayoun | |
| 2005/0112386 A1 | 5/2005 | Akiyama | |
| 2006/0151884 A1 | 7/2006 | Hara | |
| 2010/0089636 A1 | 4/2010 | Ramadas | |
| 2010/0282693 A1 | 11/2010 | Coulson | |
| 2010/0330347 A1 | 12/2010 | Badyal | |
| 2011/0114555 A1 | 5/2011 | Coulson | |
| 2011/0148050 A1 | 6/2011 | Vissing | |
| 2011/0195243 A1 | 8/2011 | Polegato Moretti | |
| 2011/0262740 A1 | 10/2011 | Martin, III | |
| 2012/0257364 A1 | 10/2012 | Brooks | |
| 2013/0040102 A1 * | 2/2013 | Gleason | B05D 1/62 |
| | | | 428/141 |
| 2013/0059105 A1 | 3/2013 | Wright | |
| 2013/0171546 A1 | 7/2013 | White | |
| 2013/0211004 A1 | 8/2013 | Coulson | |
| 2013/0240256 A1 | 9/2013 | Von Werne | |
| 2014/0006643 A1 | 1/2014 | Ur | |
| 2014/0011009 A1 | 1/2014 | Fish | |
| 2014/0186620 A1 | 7/2014 | Gleason | |
| 2014/0342954 A1 | 11/2014 | Ingber | |
| 2015/0125679 A1 | 5/2015 | Ishikawa | |
| 2015/0175814 A1 | 6/2015 | Aizenberg | |
| 2015/0196940 A1 | 7/2015 | Aizenberg | |
| 2015/0209198 A1 | 7/2015 | Aizenberg | |
| 2015/0209846 A1 | 7/2015 | Aizanberg | |
| 2015/0210951 A1 | 7/2015 | Aizenberg | |
| 2015/0237953 A1 | 8/2015 | Polegato Moretti | |
| 2015/0273522 A1 | 10/2015 | Boscher | |
| 2015/0314941 A1 | 11/2015 | Ramadas | |
| 2015/0329687 A1 | 11/2015 | Gallou | |
| 2017/0107345 A1 * | 4/2017 | Kon | C23C 16/02 |

(56) References Cited

U.S. PATENT DOCUMENTS

FOREIGN PATENT DOCUMENTS

| WO | 2005002640 | 1/2005 |
| WO | 2006005887 | 1/2006 |
| WO | 2008122292 | 10/2008 |

OTHER PUBLICATIONS

Burkey et al., "Structure and Mechanical Properties of Thin Films Deposited from 1,3,5-trimethyl-1,3,5-trivinylcyclotrisiloxane and Water" J. Appl. Phys.; Apr. 2003; vol. 93 No. 9; pp. 5143-5150.
Burkey, "Pulsed-Plasma Chemical Vapor Deposition of Organosilicon Thin Films for Dielectric Applications" Doctoral Thesis; Massachusetts Institute of Technology; May 14, 2003; 142 pages.
Coclite et al., "Initiated PECVD of Organosilicon Coatings: A New Strategy to Enhance Monomer Structure Retention" Plasma Process. Polm.; Apr. 2012; 9; pp. 425-434.
Fitzpatrick, "Implantable Electronic Medical Devices" Academic Press; Elsevier; Oct. 31, 2014; 195 pages.
Green et al., "Heterogeneous Integration for Revolutionary Microwave Circuits at DAPRA" Microwave Journal; Jun. 9, 2015; 9 pages.
International Search Report & Written Opinion for PCT/US2017/037291 dated Sep. 20, 2017.
Limb, "Pulsed Plasma Enhanced and Pyrolytic Chemical Vapor Deposition of Fluorocarbon Biopassivation Coatings" Doctoral Thesis; Massachusetts Institute of Technology; Jun. 1997; 231 pages.
Murthy et al, "Initiation of Cyclic Vinylmethylsiloxane Polymerization in a Hot-Filament Chemical Vapor Deposition Process" Langmuir; Jul. 2002; vol. 18; No. 16; pp. 6424-6428.
O'Shaughnessy et al. "Initiated Chemical Vapor Deposition of Trivinyltrimethylcyclotrisiloxane for Biomaterial Coatings" Langmuir; Jun. 30, 2006; vol. 22; No. 16; pp. 7021-7026.
O'Shaughnessy et al. "Stable Biopassive Insulation Synthesized by Initiated Chemical Vapor Deposition of Poly (1,3,5-trivinyltrimethylcyclotrisiloxane)" Biomacromolecules; Jun. 2007; vol. 8; No. 8; pp. 2564-2570.
O'Shaughnessy et al. "Functional Thin Film Polymers for Biopassivation of Neuroprosthetic Implants" Doctoral Thesis; Massachusetts Institute of Technology; May 16, 2007; 115 pages.
Trujillo et al., "Ultrlow Dielectric Constant Tetravinyltetramethylcyclotertrasiloxane Films Deposited by Initiated Chempcal Vapor Deposition (iCVD)" Adv. Func. Mater.; Jan. 2010; vol. 20; No. 4; pp. 607-616.

* cited by examiner

METHODS FOR PLASMA DEPOSITING POLYMERS COMPRISING CYCLIC SILOXANES AND RELATED COMPOSITIONS AND ARTICLES

RELATED APPLICATIONS

This application claims priority under 35 U.S.C. § 120 to PCT/US2017/037291 to GVD Corporation, filed Jun. 13, 2017, which claims priority under 35 U.S.C. § 119(e) to U.S. Provisional Patent Application Ser. No. 62/349,593, filed Jun. 13, 2016, entitled "METHODS FOR PLASMA DEPOSITING POLYMERS COMPRISING CYCLIC SILOXANES AND RELATED COMPOSITIONS AND ARTICLES". The disclosures of these applications are incorporated herein by reference in their entirety for all purposes.

FIELD

Methods for plasma depositing polymers comprising cyclic siloxanes and related articles and compositions are generally provided.

BACKGROUND

Polymers comprising cyclic siloxanes have many properties which are beneficial in coating applications. The polymers may be formed by polymerizing monomers comprising cyclic siloxane groups. Generally, a high percentage of the cyclic siloxane groups are retained when using traditional solution phase polymerization techniques. Cyclic siloxane groups may also be retained during polymerization when utilizing hot filament vapor deposition techniques, specifically in combination with a free radical initiator. However, hot filament techniques are undesirable for forming polymer coatings for commercial applications due to, for example, limitations in the types and shapes of substrates that may be coated. Use of certain existing polymerization methods, such as plasma-enhanced chemical vapor deposition (PECVD), to polymerize such monomers have shown in the past to result in the cleavage of a significant percentage of the cyclic siloxane rings and thus, the resulting polymer did not have desirable properties for certain commercial applications. Accordingly, improved methods for depositing polymers comprising cyclic siloxanes and articles which incorporate such polymers are needed.

SUMMARY

The present disclosure generally provides methods for fabricating polymers comprising cyclic siloxanes, and related compositions and articles. The subject matter of the present invention involves, in some cases, interrelated products, alternative solutions to a particular problem, and/or a plurality of different uses of one or more systems and/or articles.

In a first embodiment, a method of fabricating a polymer via a plasma-enhanced chemical vapor deposition is provided. In accordance with one set of embodiments, the method comprises flowing a precursor gas in proximity to a substrate within a PECVD reactor, wherein the precursor gas comprises an initiator and at least one monomer comprising a cyclic siloxane and at least two vinyl groups; and depositing a polymer formed from at least one monomer on at least a portion of the substrate, wherein the plasma power density of the PECVD process is less than or equal to about 15 mW/cm$^2$.

In a second embodiment, a method is provided comprises flowing a precursor gas in proximity to a substrate within a PECVD reactor, wherein the precursor gas comprises an initiator and at least one monomer comprising a cyclic siloxane and at least two vinyl groups; and depositing a polymer formed from the at least one monomer on at least a portion of the substrate, wherein the percent of the cyclic siloxane groups in the polymer is greater than or equal to about 60%, or greater than or equal to about 65%.

In a third embodiment, a device is provided comprising high frequency radio frequency (RF) device and a polymeric film formed on at least a portion of or substantially coating the high frequency RF device, wherein the polymeric film is formed via reaction of at least one monomer comprising a cyclic siloxane monomer and at least one vinyl group, wherein substantially all of the cyclic siloxane groups are retained in the polymeric film.

In a fourth embodiment, a device is provided comprising a medical device and a polymeric film formed on at least a portion of the medical device, wherein the polymeric film is formed via reaction of at least one monomer comprising a cyclic siloxane monomer and at least one vinyl group, wherein substantially all of the cyclic siloxane groups are retained in the polymeric film.

In a fifth embodiment, according to any one of the first through fourth embodiments, the monomer comprises at least two vinyl groups.

In a sixth embodiment, according to any one of the first through fifth embodiments, wherein the at least one monomer comprises one or more of trivinyltrimethylcyclotrisiloxane, tetravinyltetramethylcyclotetrasiloxane, or trivinylpentamethyltetrasiloxane.

In a seventh embodiment, according to any one of the first through sixth embodiments, wherein the at least one monomer comprises trivinyltrimethylcyclotrisiloxane.

In an eighth embodiment, according to any one of the first through seventh embodiments, wherein the percentage of the cyclic siloxane groups in the polymer and/or polymeric film is greater than or equal to about 60%, greater than or equal to about 65%, greater than or equal to about 70%, greater than or equal to about 75%, or greater than or equal to about 80%.

In a ninth embodiment, according to any one of the first through eighth embodiments, wherein the percentage of the cyclic siloxane groups in the polymer and/or polymeric film is determined by dividing the maximum absorbance of cyclic siloxane peak in an FTIR spectrum by the total of the sum of the maximum absorbance of cyclic siloxane peak plus the maximum absorbance of linear siloxane peak, and multiplying by 100%.

In a tenth embodiment, according to any one of the first through ninth embodiments, wherein the polymer is formed as a film on a portion of the surface of the substrate.

In an eleventh embodiment, according to any one of the first through tenth embodiments, wherein the film and/or polymeric film has thickness of greater than or equal to 50 nm and less than or equal to 10 um.

In a twelfth embodiment, according to any one of the first through eleventh embodiments, wherein the film and/or polymeric film has a dielectric constant of less than or equal to 3.

In an thirteenth embodiment, according to any one of the first through twelfth embodiments, wherein the initiator comprises a peroxide.

In a fourteenth embodiment, according to any one of the first through thirteenth embodiments, wherein the initiator comprises tert-butyl peroxide and/or the peroxide is tert-butyl peroxide.

In a fifteenth embodiment, according to any one of the first through fourteenth embodiments, wherein the initiator comprises tert-amyl peroxide and/or the peroxide is tert-amyl peroxide.

In a sixteenth embodiment, according to any one of the first through fifteenth embodiments, wherein the precursor gas further comprises at least one inert gas.

In a seventeenth embodiment, according to any one of the first through sixteenth embodiments, wherein the substrate comprises one or more of gold, copper, solder, solder flux, indium phosphide, gallium sulfide, gallium nitride, and silicon.

In an eighteenth embodiment, according to any one of the first through seventeenth embodiments, wherein the high frequency RF device comprises one or more of a metal-insulator-metal capacitor (MIMC), a transmission line, a filter, and an oscillator.

In a nineteenth embodiment, according to any one of the first through eighteenth embodiments, wherein the high frequency RF device comprises one or more of a complementary metal-oxide-semiconductor (CMOS) substrate, a printed circuit board, a flexible circuit, an electronic circuit, and/or an electronic chip.

In a twentieth embodiment, according to any one of the first through nineteenth embodiments, wherein the electronic chip comprises two or more materials that are heterogeneously integrated.

In a twenty first embodiment, according to any one of the first through twentieth embodiments, wherein the RF device comprises an output for a given input which varies by less than about 25% as compared to a substantially similar device not comprising the polymeric film.

In a twenty second embodiment, according to any one of the first through twenty first embodiments, wherein the input signal is between about 0.1 and about 100 GHz.

In a twenty third embodiment, according to any one of the first through twenty second embodiments, wherein the polymeric film changes an output from the device in the range of 10-100 GHz by less than about 10% for a given input as compared to a substantially similar device that does not comprise the polymeric film.

In a twenty fourth embodiment, according to any one of the first through twenty third embodiments, wherein the polymeric film changes an output from the device in the range of 10-100 GHz by less than about 5% for a given input as compared to a substantially similar device that does not comprise the polymeric film.

In a twenty-fifth embodiment, according to any one of the first through twenty-fourth embodiments, wherein the polymeric film is a thin film.

In a twenty-sixth embodiment, according to any one of the first through twenty-fifth embodiments, wherein the RF device comprises two or more materials that are heterogeneously integrated.

In a twenty-seventh embodiment, according to any one of the first through twenty-sixth embodiments, wherein the RF device comprises one or more of silicon, indium phosphide, and gallium nitride.

In a twenty-eighth embodiment, according to any one of the first through twenty-seventh embodiments, wherein the RF device comprises one or more of includes indium tin oxide, fluorine tin oxide, antimony-doped tin oxide, glassy carbon, carbon mesh, platinum oxide, nickel oxide, zinc oxide, tin oxide, vanadium oxide, zinc-tin oxide, indium oxide, indium-zinc oxide, graphite, a zeolite, gold, copper, silver, platinum, ruthenium, rhodium, osmium, iridium, nickel, cadmium, tin, lithium, chromium, calcium, titanium, aluminum, cobalt, zinc, vanadium, nickel, palladium, quartz, glass, polyethylene terephthalate, polyethylene naphthalate, polycarbonate, polystyrene, polypropylene, aluminum nitride, silicon carbide, gallium sulfide, and gallium arsenide.

In a twenty-ninth embodiment, according to any one of the first through twenty-eighth embodiments, wherein the polymeric film comprises a peroxide.

In a thirtieth embodiment, according to any one of the first through twenty-ninth embodiments, wherein the polymeric film comprises tert-butyl peroxide and/or the peroxide is tert-butyl peroxide.

In a thirty-first embodiment, according to any one of the first through thirtieth embodiments, wherein the polymeric film comprises tert-amyl peroxide and/or the peroxide is tert-amyl peroxide.

In a thirty-second embodiment, according to any one of the first through thirty-first embodiments, wherein the film and/or polymeric film is capable of passing one or more of the MIL-I-46058C, IPC-CC-830 Rev B, MIL-STD-810G method 507.5, MIL-STD-810G method 509.5, JESD 22A100D, JESD 22A101C, JESD 22A110D, and ASTM B117 tests.

In a thirty-third embodiment, according to any one of the first through thirty-second embodiments, wherein the film and/or polymeric film is capable of passing one or more of the MIL-I-46058C, IPC-CC-830 Rev B, MIL-STD-810G method 507.5, MIL-STD-810G method 509.5, JESD 22A100D, JESD 22A101C, JESD 22A110D, and ASTM B117 tests after undergoing a percent elongation of greater than or equal to 1%.

In a thirty-fourth embodiment, according to any one of the first through thirty-third embodiments, wherein the medical device comprises one or more of a retinal implant, a retinal prostheses, a smart contact lens, a phrenic nerve stimulator, a breathing pacemaker system, a diaphragm pacing system, an implantable glucose sensor, a cochlear implant, a pacemaker, a defibrillator, a sacral anterior root stimulator, an occipital nerve stimulator, a spinal cord stimulator, a deep brain stimulator, a neurostimulator, a vagus nerve stimulator, a drop foot stimulator, a handgrip stimulator, an implantable pump, an electromagnetic micropump, an osmotic micropump, an electro-osmotic micropump, an electrolysis micropump, a constant flow infusion pump, an ophthalmic micropump, and a wireless microchip drug delivery system.

In an thirty fifth embodiment, according to any one of the first through thirty fourth embodiments, wherein the film and/or polymeric film comprises a dielectric breakdown voltage of greater than or equal to 3500 V/mil.

In a thirty sixth embodiment, according to any one of the first through thirty fifth embodiments, wherein the film and/or polymeric film has a water vapor permeability of greater than or equal to 500 g/m$^2$/day.

Other advantages and novel features of the present invention will become apparent from the following detailed description of various non-limiting embodiments of the invention when considered in conjunction with the accompanying figures. In cases where the present specification and a document incorporated by reference include conflicting and/or inconsistent disclosure, the present specification shall control. If two or more documents incorporated by reference include conflicting and/or inconsistent disclosure with respect to each other, then the document having the later effective date shall control.

BRIEF DESCRIPTION OF THE DRAWINGS

Non-limiting embodiments of the present invention will be described by way of example with reference to the accompanying figures, which are schematic and are not intended to be drawn to scale. In the figures, each identical or nearly identical component illustrated is typically represented by a single numeral. For purposes of clarity, not every component is labeled in every figure, nor is every component of each embodiment of the invention shown where illustration is not necessary to allow those of ordinary skill in the art to understand the invention. In the figures.

DETAILED DESCRIPTION

Figure 1A:
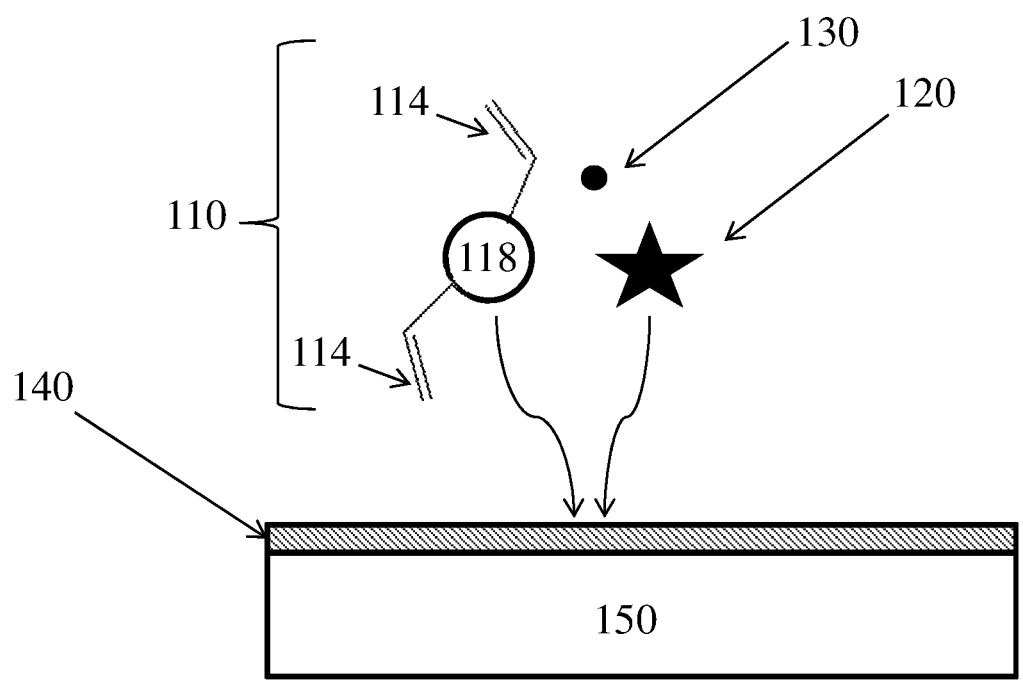
FIG. 1A shows, in accordance with some embodiments, a schematic illustration of a method of fabricating a polymer via a plasma-enhanced chemical vapor deposition (PECVD) process.

The present disclosure generally provides methods for plasma depositing polymers comprising cyclic siloxanes and related compositions and articles.

As will be known to those of skill in the art, monomers comprising cyclic siloxanes and vinyl groups may be polymerized using a variety of methods. Depending on the polymerization method employed, the polymerization may proceed via a variety of mechanisms, for example, via reaction of the vinyl group and/or cleavage of the cyclic siloxanes to form polymers comprising linear siloxane groups. The properties of the synthesized polymers vary depending on the amount of the cyclic siloxanes cleaved during polymerization. For many applications, it is highly desirable to utilize methods that minimize cleavage of the cyclic siloxanes. For example, use of hot filament vapor deposition techniques can result in polymers wherein a significant portion of the cyclic siloxanes are retained, especially when free radical initiators are utilized, and the majority of the polymerization occurs via reaction of the vinyl groups. In contrast, known techniques involving plasma processes have shown in the past to result in a significant portion of the cyclic siloxane rings being cleaved.

The methods described herein relate to the use of plasma-enhanced chemical vapor deposition (PECVD) to polymerize monomers comprising cyclic siloxanes, wherein a significant portion of the cyclic siloxane rings are retained. In some embodiments, a method comprises flowing a precursor gas comprising at least one initiator and at least one monomer comprising a cyclic siloxane and at least two vinyl groups in proximity to a substrate within a PECVD reactor, whereby the monomer polymerizes on at least a portion of a surface of the substrate, wherein the PECVD conditions are selected so as to retain a significant percentage of the cyclic siloxane rings present in the monomer. Advantageously, the methods and articles described herein may offer one or more advantages over certain existing methods for plasma deposition of monomers comprising cyclic siloxanes including, but not limited to, retention of a significant portion of the cyclic siloxanes present in the monomers in the resulting polymers.

The presence of a significant portion of the cyclic siloxanes in the polymers results in articles that have superior properties as compared to polymers which do not retain a significant portion of the cyclic siloxanes, for example, superior protective, dielectric, and/or mechanical properties. Accordingly, in some embodiments, polymers formed by the methods described herein have properties that are beneficial for coating applications wherein the coating functions as environmental protection coating. For example, polymers formed by the methods described herein may comprise a low number of defects, such as pinholes and/or cracks, or may be substantially defect-free. In some embodiments, the polymers formed by the methods described herein may provide protection for devices against environmental contaminants such as moisture and/or salt, thereby reducing or preventing, for example, undesirable corrosion and short circuiting. According to certain embodiments, the polymers formed by the methods described herein may be able to further provide protection against mechanical damage from, e.g., loose metallic debris on circuitry. The polymers may also have desirable physical properties, such as a low dielectric constant and/or high resistance to damage during mechanical deformation. These properties may allow the polymers to act as insulators and/or be able to retain their initial beneficial properties after undergoing bending or elongation. For these reasons, films comprising cyclic siloxanes may be suited for applications such as coatings for chip die, chip packages, full circuit boards, electronic circuits, RF circuits, printed circuit boards, CMOS chips, and/or medical devices. In certain embodiments, films comprising cyclic siloxanes may be capable of serving as a replacement for hermetic packaging for these or other substrates. Additional details are described herein.

Using PECVD to fabricate polymers comprising cyclic siloxanes may provide benefits as compared to other methods of synthesis. For example, PECVD may allow for the deposition of polymers with the target chemistry at higher rates than other methods, and/or may allow for the use of different deposition rates during the deposition process so that the steps of initial polymer formation on the substrate and growth from the initially deposited material can be optimized separately. PECVD may thus allow for the fabrication of films comprising cyclic siloxanes at rates that are commercially valuable which also comprise the beneficial properties described above. PECVD may also allow for more conformal coverage of a 3D coating substrate than alternate coating approaches, i.e. liquid based coating techniques or hot filament CVD.

A non-limiting example of a method for fabricating a polymer comprising cyclic siloxanes is shown illustratively in FIG. 1A. The method comprises flowing a precursor gas in close proximity to a substrate in a PECVD reactor, exposing the precursor gas to plasma 130 such that a polymerization reaction occurs which results in the deposition of polymer 140 on at least a portion of substrate 150.

Figure 1B:
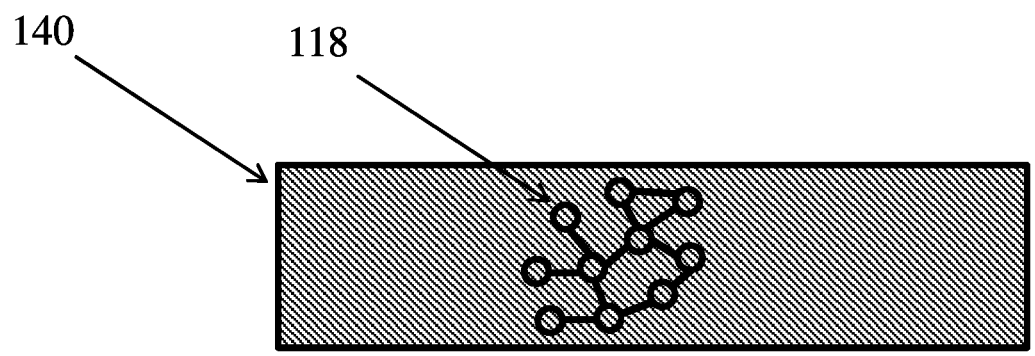
FIG. 1B shows according to certain embodiments, a schematic illustration of a polymer fabricated via a plasma-enhanced chemical vapor deposition (PECVD) process.

The precursor gas may comprise at least one monomer 110 comprising cyclic siloxane group 118 and two vinyl groups 114, and initiator 120. In some embodiments, initiator 120 comprises a free radical initiator. The polymer 140 formed by this process may comprise the at least one monomer. In some embodiments, the polymerization reaction can comprise polymerization of one or more of the vinyl groups 114 by any suitable means, for example, free radical polymerization. This polymerization reaction can, according to some embodiments, result in the formation of crosslinked polymer 140 comprising cyclic siloxane 118, as shown illustratively in FIG. 1B In some embodiments, the polymer may be formed via polymerization of one or more types of monomers. In some embodiments, one type of monomer is polymerized, two types or monomers are polymerized, or three or more types of monomers are polymerized. Generally, at least one type of monomer comprises a cyclic siloxane group. The term cyclic siloxane is given its ordinary meaning in the art and refers to an organosilicon compound comprising a suitable cyclic moiety of the structure $[-Si(R)_2-O-]_m$, wherein m is 3, 4, 5, 6, or more, and R is any suitable group. In some embodiments, each type of monomer comprises a cyclic siloxane group. Those of ordinary skill in the art will be aware of suitable monomers comprising cyclic siloxane groups. In some embodiments, a monomer comprises three siloxane repeat units, four siloxane repeat units, five siloxane repeat units, six siloxane repeat units, or more. In some embodiments, a monomer comprises at one or more vinyl groups. In some embodiments, the monomers may comprise one vinyl group, two vinyl groups, three vinyl groups, or four vinyl groups. In some embodiments, a monomer comprises two vinyl groups. In some embodiments, a monomer comprises three vinyl groups. A non-limiting example of a monomer comprising a cyclic siloxane group has the structure of Formula (I):

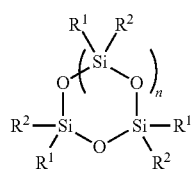

(I)

wherein each $R^1$ and $R^2$ is the same or different and is independently substituted or unsubstituted alkyl or substituted or unsubstituted alkene, and n is 1, 2, 3, 4, 5, or 6, or may comprise a bond to another linear or cyclic siloxane (e.g., $R^1$ or $R^2$ may be —O—Si—). In some embodiments, each $R^1$ and $R^2$ is the same or different is unsubstituted alkyl or is unsubstituted alkene, and n is 1, 2, 3, 4, 5, or 6. In some embodiments, at least one $R^1$ or $R^2$ is unsubstituted alkene (e.g., vinyl). In some embodiments, at least two $R^1$ and/or $R^2$ is unsubstituted alkene (e.g., vinyl). In some embodiments, at least three $R^1$ and/or $R^2$ is unsubstituted alkene (e.g., vinyl). In some embodiments, each $R^1$ is unsubstituted alkyl and each $R^2$ is unsubstituted alkene. In some embodiments, each $R^1$ comprises at least one Si—O bond and each $R^2$ is unsubstituted alkene. In some embodiments, each $R^1$ is methyl and each $R^2$ is vinyl. In some embodiments, n is 1. In some embodiments, n is 2. In some embodiments, n is 3. In some embodiments, n is 4. In some embodiments, n is 1, each $R^1$ is methyl and each $R^2$ is vinyl (i.e., $CHCH_2$). In some embodiments, n is 1, each $R^1$ is methyl and each $R^2$ is vinyl. Non-limiting examples on monomers comprising a cyclic siloxane and at least two vinyl groups are trivinyltrimethylcyclotrisiloxane, tetravinyltetramethylcyclotetrasiloxane, and trivinylpentamethyltrisiloxane, for example:

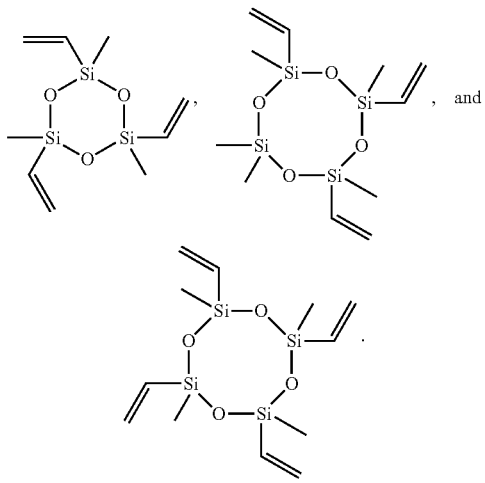

As used herein, the term polymer is given its ordinary meaning in the art. A polymer is generally composed of one or more monomers or "repeat units," which are chemically bonded together in some fashion. It should be understood that the polymer formed comprising the monomers described herein or formed from the monomers described herein may comprise other components. In addition, as would be understood by a person of skill in the art, the monomer generally undergoes a chemical modification during the polymerization process, and thus, one or more of the bonds present in the monomer may not be present in the polymer.

Monomers comprising a cyclic siloxane ring and at least two vinyl groups may be polymerized using the methods described herein. In some embodiments, the monomers may be polymerized using methods wherein a significant portion (e.g., greater than about 50%, or more, as described herein) of the cyclic siloxane rings are retained in the polymer, whereby polymerization occurs primarily via reaction of the vinyl groups. Following polymerization of the monomer(s), the percentage of cyclic siloxane rings present in a polymer can be measured using any suitable technique known in the art. For example, in some embodiments, the percent of cyclic siloxane rings in a polymer may be measured using spectroscopic techniques, for example, Fourier Transform Infrared Spectroscopy (FTIR) and/or Nuclear Magnetic Resonance (NMR). In certain embodiments, the percent of cyclic siloxane rings may be determined by measuring the FTIR spectrum for a polymer film, determining the thickness of the polymer film, and then normalizing the FTIR spectrum based on the thickness of the polymer film. The thickness of the polymer film may be determined using any method known to those of ordinary skill in the art. In some embodiments, the thickness of the polymer film may be determined using profilometry. For films that are disposed on substrates, the FTIR spectrum for the polymer film is typically corrected to account for signals arising from the substrate. This correction can be performed by measuring a background spectrum, such as the spectrum of an otherwise identical substrate lacking a polymer film, and then subtracting the background spectrum from the spectrum measured for sample containing both the polymer film and the substrate.

The percent of cyclic siloxanes present in the polymer relative to the total amount of siloxanes in the polymer (e.g., cyclic siloxanes and linear siloxanes) based on IR intensities described herein is determined via the following equation:

$$\text{Percent cyclic siloxane in polymer} = \frac{\text{maximum absorbance of cyclic siloxane peak}}{\left(\begin{array}{c}\text{maximum absorbance of cyclic siloxane peak} + \\ \text{maximum asorbance of linear siloxane peak}\end{array}\right)} \times 100\%$$

The maximum absorbance of the cyclic siloxane peak is the maximum absorbance between about 1105 cm$^{-1}$ and about 1120 cm$^{-1}$ in an FTIR spectrum. The maximum absorbance of the linear siloxane peak is the maximum absorbance between about 1070 cm$^{-1}$ and about 1105 cm$^{-1}$ in an FTIR spectrum. In some embodiments, the percent cyclic siloxane in the polymer formed by the methods described herein may be greater than or equal to 50%, greater than or equal to 60%, greater than or equal to 65%, greater than or equal to 66%, greater than or equal to 67%, greater than or equal to 70%, greater than or equal to 80%, greater than or equal to 90%, greater than or equal to 95%, or greater than or equal to 99%. In some embodiments, the percent cyclic siloxane in the polymer formed by the methods described herein may be less than or equal to 100%, less than or equal to 99%, less than or equal to 98%, less than or equal to 95%, less than or equal to 90%, less than or equal to 80%, less than or equal to 70%, less than or equal to 67%, less than or equal to 66%, less than or equal to 65%, or less than or equal to 60%. Combinations of the above-referenced ranges are also possible. In some embodiments, the percent cyclic siloxane in the polymer formed by the methods described herein may be between about 50% and about 99%, between about 60% and about 99%, between about 65% and about 90%, between about 66% and about 90%, between about 67% and about 90%, between about 70% and about 99%, or between about 80% and about 99%.

Figure 2A:
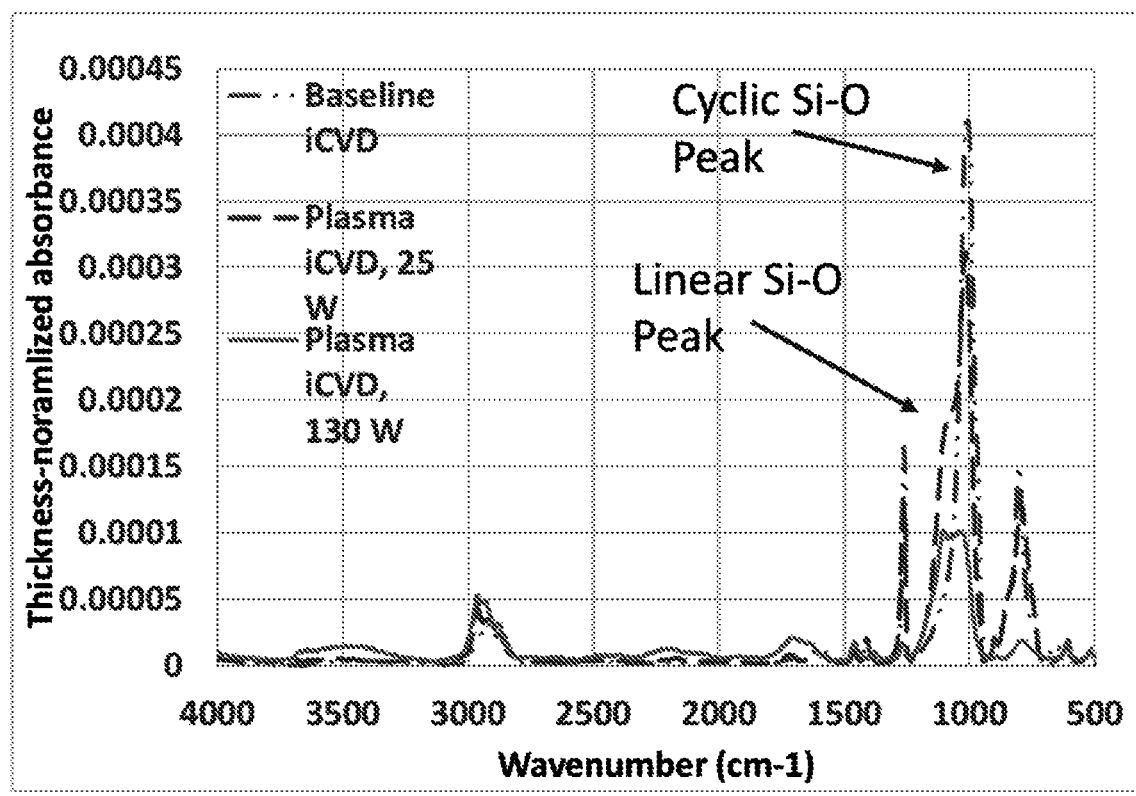
FIG. 2A shows, according to some embodiments, the Fourier Transform Infrared (FTIR) spectra of non-limiting films deposited via a variety of methods.
Figure 2B:
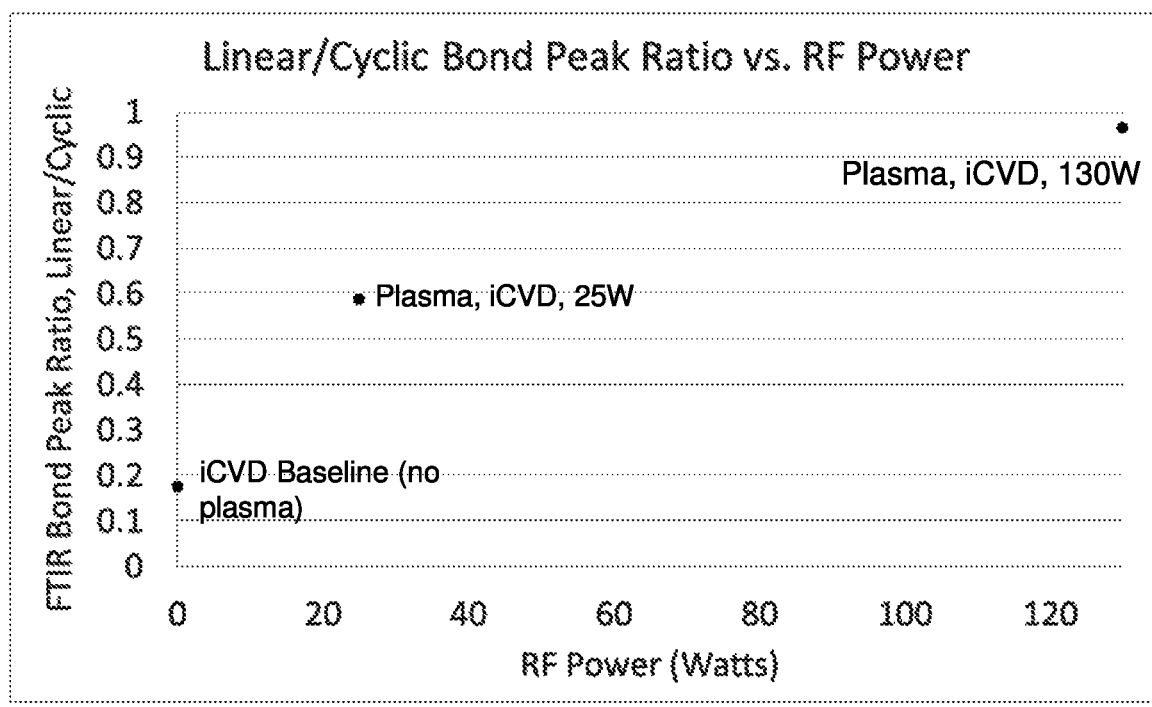
FIG. 2B shows, in accordance with certain embodiments, a chart showing the ratios of cyclic siloxane absorbance to linear siloxane absorbance for non-limiting films deposited via a variety of methods.

FIG. 2A shows exemplary thickness-normalized FTIR spectra from polymers synthesized using three different methods—a polymer prepared via iCVD with no plasma present, in which the majority of the cyclic siloxane groups are retained, PECVD in the presence of 25 W plasma and conditions described herein, and PECVD the presence of a 130 W plasma. The percent of cyclic siloxane rings for each of these polymers could be determined in the manner described above. FIG. 2B shows the ratio of the maximum linear siloxane absorption peak to the maximum cyclic siloxane absorption peak for each of these three methods.

In embodiments wherein the monomers comprise at least one vinyl group, at least a portion of the vinyl groups react during the polymerization process and thus, the resulting polymer comprises a fewer vinyl groups. A person of skill in the art will be aware of methods for determining the percentage of vinyl groups retained in the polymer as compared to the total amount of monomer used to form the polymer. For example, the percentage may be determined by dividing the number of vinyl groups present in the polymer (e.g., determined by NMR, FTIR, or other techniques) by the number of vinyl groups present in the monomers utilized to form the polymer multiplied by 100%. For example, FTIR can be used to measure the absorbance characteristic of a vinyl group (e.g., the C=C double bond stretch, which absorbs at 1597 cm$^{-1}$) after polymerization of the monomer. FTIR measurements may be made on polymer films, normalized by the film thickness, and corrected for signals arising from the substrate, as described above in relation to the determination of the cyclic and linear siloxane absorbances of polymer films. The vinyl absorption of the monomer may be determined by consulting a standard database, such as that available at NIST, or by performing an FTIR measurement on the monomer.

The percentage of vinyl groups retained in the polymer based on IR intensities described herein is determined via the following equation:

$$\text{Percent of vinyl groups retained} = \frac{\text{absorbance of C=C double bond stretch in the polymer film}}{\text{absorbance of C=C double bond stretch in the monomer prior to polymerization}} \times 100\%.$$

According to some embodiments, the polymer may comprise a percentage of monomer vinyl groups retained that is less than or equal to 60%, less than or equal to 50%, less than or equal to 40%, less than or equal to 30%, less than or equal to 20%, less than or equal to 10%, or less than or equal to 5%. Other ranges are also possible.

In some embodiments, the polymers described herein may be formed by vapor deposition, which may comprise the introduction of one or more reagents in the vapor phase and/or polymerization reactions which occur between molecules in the vapor phase. Likewise, the polymerization processes described herein may refer to a vapor deposition process. In some embodiments, vapor deposition may have advantages over other methods of polymer formation, such as allowing for conformal coating of substrates, allowing for simultaneous polymerization and film formation, and/or reducing the need for solvents or other species which may be necessary for other methods of polymer formation.

Polymerization may occur under conditions comprising one or more monomers at any suitable partial pressure. In some embodiments, any of the one or more monomer may be at a partial pressure of less than or equal to 300 mTorr, 200 mTorr, 100 mTorr, 75 mTorr, less than or equal to 50 mTorr, less than or equal to 30 mTorr, less than or equal to 20 mTorr, less than or equal to 15 mTorr, less than or equal to 10 mTorr, less than or equal to 5 mTorr, or less than or equal to 3 mTorr. In some embodiments, the partial pressure is less than 50 mTorr. In some embodiments, the partial pressure is about 5 mTorr. According to certain embodiments, any of the one or more monomers may be at a partial pressure of greater than or equal to 1 mTorr, greater than or equal to 5 mTorr, greater than or equal to 10 mTorr, or greater than or equal to 20 mTorr. Combinations of the above-referenced ranges are also possible (e.g., greater than or equal to 3 mTorr and less than or equal to 50 mTorr, greater than or equal to 1 mTorr and less than or equal to 50 mTorr, greater than or equal to 1 mTorr and less than or equal to 20 mTorr, greater than or equal to 3 mTorr and less than or equal to 10 mTorr). Other ranges are also possible.

In certain embodiments, the polymerization of the monomers may be initiated by one or more initiators. In some embodiments, initiator(s) may comprise one or more groups which are capable of generating free radicals under the experimental conditions. In accordance with some embodiments, such free radicals may be capable of reacting with monomers to form growing polymer chains. According to certain embodiments, initiators may be capable of decomposing to form one or more molecules comprising a free radical. In certain embodiments, initiators may comprise functional groups which are capable of forming radicals under the experimental conditions (e.g., by decomposing). Non-limiting examples of suitable functional groups include peroxide groups, persulfate groups, and azo groups. In some embodiments, the initiator may comprise one or more of tert-butyl peroxide and tert-amyl peroxide.

In some embodiments, polymerization may occur in the presence of one or more initiators. Without wishing to be bound by theory, it is believed that the presence of initiator(s) may promote the retention of siloxane rings by allowing for polymerization to occur under mild reaction conditions. Initiators which comprise free radical groups or which are capable of undergoing a reaction to form free radical groups may be particularly advantageous. The initiator(s) may be present at any suitable partial pressure. In some embodiments, the initiator(s) may be at a partial pressure of less than or equal to 300 mTorr, 200 mTorr, 100 mTorr, 75 mTorr, less than or equal to 50 mTorr, less than or equal to 30 mTorr, less than or equal to 20 mTorr, less than or equal to 15 mTorr, less than or equal to 10 mTorr, less than or equal to 5 mTorr, or less than or equal to 3 mTorr. According to certain embodiments, the initiator(s) may be at a partial pressure of greater than or equal to 1 mTorr, greater than or equal to 5 mTorr, greater than or equal to 10 mTorr, or greater than or equal to 20 mTorr. In some embodiments, the partial pressure of the monomer is less than about 75 mTorr. In some embodiments, the partial pressure of the initiator is about 7.5 mTorr. Combinations of the above-referenced ranges are also possible (e.g., greater than or equal to 1 mTorr and less than or equal to 75 mTorr, or greater than or equal to 1 mTorr and less than or equal to 50 mTorr, greater than or equal to 1 mTorr and less than or equal to 20 mTorr, greater than or equal to 1 mTorr and less than or equal to 10 mTorr, greater than or equal to 5 mTorr and less than or equal to 10 mTorr). Other ranges are also possible.

The one or more monomers and initiator may be provided in any suitable ratio. In some embodiments, the ratio may be based on the partial pressures of the monomer(s) to the initiator. The ratio of the partial pressure of the initiator(s) to the partial pressure of the monomers, defined as the partial pressure of the initiators divided by the partial pressure of the monomers, may be any suitable value. In accordance with certain embodiments, the ratio of the partial pressure of the initiators to the partial pressure of the monomers may be greater than or equal to 0.1, greater than or equal to 0.2, greater than or equal to 0.5, greater than or equal to 0.8, greater than or equal to 1, greater than or equal to 2, greater than or equal to 5, or greater than or equal to 8. In some embodiments, the ratio of the partial pressure of the initiators to the partial pressure of the monomers may be less than or equal to 10, less than or equal to 8, less than or equal to 5, less than or equal to 2, less than or equal to 1, less than or equal to 0.8, less than or equal to 0.5, or less than or equal to 0.2. Combinations of the above-referenced ranges are also possible (e.g., greater than or equal to 0.1 and less than or equal to 10). Other ranges are also possible.

According to certain embodiments, polymerization may occur in the presence of one or more gases which do not participate in the polymerization. In some embodiments, such gases may be inert gases. In some embodiments, one type of inert gas, two types of inert gases, three types of inert gases, or more, may be present during polymerization. Non-limiting examples of inert gases include nitrogen, helium, and argon. The inert gases may comprise any suitable percentage of the total pressure during polymerization. Total pressure during polymerization may be defined as the sum of the partial pressures of the monomer(s), initiator(s), and inert gas(es) present during polymerization. In some embodiments, the inert gas(es) comprise greater than or equal to 50% of the total pressure, greater than or equal to 60% of the total pressure, greater than or equal to 70% of the total pressure, greater than or equal to 80% of the total pressure, greater than or equal to 90% of the total pressure, or greater than or equal to 95% of the total pressure. According to certain embodiments, the inert gas(es) comprise less than or equal to 98% of the total pressure, less than or equal to 95% of the total pressure, less than or equal to 90% of the total pressure, less than or equal to 80% of the total pressure, less than or equal to 70% of the total pressure, or less than or equal to 60% of the total pressure. Combinations of the above-referenced ranges are also possible (e.g., greater than or equal to 50% of the total pressure and less than or equal to 90% of the total pressure, greater than or equal to 70% of the total pressure and less than or equal to 90% of the total pressure, or greater than or equal to 80% of the total pressure and less than or equal to 90% of the total pressure). Other ranges are also possible.

In certain embodiments, the total pressure of all of the species (e.g., monomer(s), initiator(s), inert gas(es)) present during polymerization fall within a specified range. In some embodiments, the total pressure of all species present during polymerization is greater than or equal to 10 mTorr, greater than or equal to 25 mTorr, greater than or equal to 50 mTorr, greater than or equal to 75 mTorr, greater than or equal to 100 mTorr, greater than or equal to 200 mTorr, greater than or equal to 200 mTorr, greater than or equal to 300 mTorr, greater than or equal to 400 mTorr, greater than or equal to 500 mTorr, greater than or equal to 750 mTorr, greater than or equal to 1000 mTorr, or greater than or equal to 2500 mTorr. According to certain embodiments, the total pressure of all species present during polymerization is less than or equal to 5000 mTorr, less than or equal to 2500 mTorr, less than or equal to 1000 mTorr, less than or equal to 750 mTorr, less than or equal to 500 mTorr, less than or equal to 400 mTorr, less than or equal to 300 mTorr, less than or equal to 200 mTorr, less than or equal to 100 mTorr, less than or equal to 75 mTorr, less than or equal to 50 mTorr, or less than or equal to 25 mTorr. Combinations of the above-referenced ranges are also possible (e.g., greater than or equal to 50 mTorr and less than or equal to 5000 mTorr, greater than or equal to 50 mTorr and less than or equal to 300 mTorr, greater than or equal to 50 mTorr and less than or equal to 200 mTorr, greater than or equal to 75 mTorr and less than or equal to 200 mTorr, or greater than or equal to 75 mTorr and less than or equal to 100 mTorr). In some embodiments, the total pressure of all species present during polymerization may be atmospheric pressure. Other ranges are also possible.

In accordance with some embodiments, polymerization may occur in the presence of a plasma. In certain embodiments, the plasma may be a phase of matter which may comprise particles which are charged and/or comprise a free radical. Without wishing to be bound by theory, the presence of plasma during polymerization may provide energy that aids in initiator and/or monomer fragmentation. In certain embodiments, the plasma may be provided in the form of a wave. In some embodiments, the plasma may be at a ratio frequency. According to certain embodiments, the plasma may be at a frequency of greater than or equal to 3 MHz, greater than or equal to 5 MHz, greater than or equal to 7.5

MHz, greater than or equal to 10 MHz, greater than or equal to 12.5 MHz, greater than or equal to 15 MHz, greater than or equal to 17.5 MHz, greater than or equal to 20 MHz, greater than or equal to 25 MHz, greater than or equal to 30 MHz, greater than or equal to 35 MHz, or greater than or equal to 40 MHz. In some embodiments, the plasma may be at a frequency of less than or equal to 50 MHz, less than or equal to 35 MHz, less than or equal to 30 MHz, less than or equal to 25 MHz, less than or equal to 20 MHz, less than or equal to 17.5 MHz, less than or equal to 15 MHz, less than or equal to 12.5 MHz, less than or equal to 10 MHz, less than or equal to 7.5 MHz, or less than or equal to 5 MHz. Combinations of the above-referenced ranges are also possible (e.g., greater than or equal to 7.5 MHz and less than or equal to 20 MHz, greater than or equal to 10 MHz and less than or equal to 15 MHz, or greater than or equal to 10 MHz and less than or equal to 20 MHz). Other ranges are also possible. In some embodiments, changes in plasma frequency may assist to provide uniform coating coverage over 3D substrates.

In certain embodiments, the plasma may be supplied in the form of one or more pulses. Pulses may occur at any frequency. In some embodiments, the plasma may be supplied in the form of pulses with a frequency of greater than or equal to 0.25 kHz, greater than or equal to 0.5 kHz, greater than or equal to 0.75 kHz, greater than or equal to 1 kHz, greater than or equal to 1.5 kHz, greater than or equal to 2 kHz, greater than or equal to 3 kHz, greater than or equal to 5 kHz, greater than or equal to 7.5 kHz, greater than or equal to 10 kHz, greater than or equal to 15 kHz, greater than or equal to 25 kHz, greater than or equal to 50 kHz, or greater than or equal to 75 kHz. In accordance with certain embodiments, the plasma may be supplied in the form of pulses with a frequency of less than or equal to 100 kHz, less than or equal to 75 kHz, less than or equal to 50 kHz, less than or equal to 25 kHz, less than or equal to 15 kHz, less than or equal to 10 kHz, less than or equal to 7.5 kHz, less than or equal to 5 kHz, less than or equal to 3 kHz, less than or equal to 2 kHz, less than or equal to 1.5 kHz, less than or equal to 1 kHz, less than or equal to 0.75 kHz, or less than or equal to 0.5 kHz. Combinations of the above-referenced ranges are also possible (e.g., greater than or equal to 0.5 kHz and less than or equal to 10 kHz, greater than or equal to 1 kHz and less than or equal to 15 kHz, or greater than or equal to 1 kHz and less than or equal to 10 kHz). Other ranges are also possible.

In accordance with some embodiments, the plasma may be supplied in the form of pulses which comprise a duty cycle. A duty cycle may be defined as the amount of time for which the plasma is applied divided by the total cycle time (the sum of the time for which the plasma is applied and the time for which the plasma is not applied). Any suitable duty cycle may be employed. According to certain embodiments, the plasma may be supplied in the form of pulses which comprise a duty cycle of greater than or equal to 0.02, greater than or equal to 0.05, greater than or equal to 0.1, greater than or equal to 0.2, greater than or equal to 0.3, greater than or equal to 0.4, or greater than or equal to 0.5. In some embodiments, the plasma may be supplied in the form of pulses which comprise a duty cycle of less than or equal to 0.75, less than or equal to 0.5, less than or equal to 0.4, less than or equal to 0.3, less than or equal to 0.2, less than or equal to 0.1, or less than or equal to 0.05. Combinations of the above—referenced ranges are also possible (e.g., greater than or equal to 0.05 and less than or equal to 0.2). Other ranges are also possible. In some embodiments, the plasma is supplied at a constant intensity throughout the polymerization.

In some embodiments, the plasma may be supplied from a plasma source, such as a plasma electrode (alternatively referred to as an active electrode). A plasma may be applied to a substrate at any suitable distance from the substrate, which is typically located directly on or proximate to a ground electrode. In some instances, the substrate is not located directly on or proximate to the ground electrode but is located for example, in between the active electrode and the ground electrode, such as by hanging the substrate in between the two electrodes. In certain embodiments, the plasma may be supplied from a plasma electrode at a distance from the substrate and/or ground electrode of greater than or equal to 1 cm, greater than or equal to 3 cm, greater than or equal to 5 cm, greater than or equal to 8 cm, greater than or equal to 10 cm, greater than or equal to 15 cm, greater than or equal to 20 cm, greater than or equal to 25 cm, greater than or equal to 30 cm, greater than or equal to 40 cm, or greater than or equal to 50 cm. In accordance with some embodiments, the plasma may be supplied from a plasma electrode at a distance from the substrate and/or ground electrode of less than or equal to 50 cm, less than or equal to 40 cm, less than or equal to 30 cm, less than or equal to 25 cm, less than or equal to 20 cm, less than or equal to 15 cm, less than or equal to 10 cm, less than or equal to 8 cm, less than or equal to 5 cm, or less than or equal to 3 cm. Combinations of the above-referenced ranges are also possible (e.g., greater than or equal to 1 cm and less than or equal to 30 cm, greater than or equal to 3 cm and less than or equal to 25 cm, or greater than or equal to 8 cm and less than or equal to 50 cm). Other ranges are also possible.

In some embodiments, the substrate may have a greatest dimension (e.g. length, width, or diameter) of about 0.1 cm, 0.5 cm, 1 cm, 5 cm, 10 cm, 15 cm, 20 cm, 25 cm, 30 cm, 35 cm, 40 cm, 45 cm, 50 cm, or greater. The substrate may have a substrate area in a range of between about 0.5-2000 $cm^2$, 1-2000 $cm^2$, 1-1500 $cm^2$, 1-1000 $cm^2$, 1-750 $cm^2$, 1-500 $cm^2$, 1-250 $cm^2$, 1-100 $cm^2$, 1-50 $cm^2$, 1-25 $cm^2$, or 1-10 $cm^2$. Other ranges are also possible. In some instances, the substrate may have a substrate area of about 2000 $cm^2$, 1900 $cm^2$, 1800 $cm^2$, 1700 $cm^2$, 1600 $cm^2$, 1500 $cm^2$, 1400 $cm^2$, 1300 $cm^2$, 1200 $cm^2$, 1100 $cm^2$, 1000 $cm^2$, 900 $cm^2$, 800 $cm^2$, 700 $cm^2$, 600 $cm^2$, 500 $cm^2$, 400 $cm^2$, 300 $cm^2$, 200 $cm^2$, or 100 $cm^2$.

The plasma or active electrode may have a greatest dimension (e.g. length, width, or diameter) of about 0.1 cm, 0.5 cm, 1 cm, 5 cm, 10 cm, 15 cm, 20 cm, 25 cm, 30 cm, 35 cm, 40 cm, 45 cm, 50 cm, or greater. The plasma or active electrode may have an area in a range of between about 0.5-10000 $cm^2$, 0.5-9000 $cm^2$, 0.5-8000 $cm^2$, 0.5-7000 $cm^2$, 0.5-6000 $cm^2$, 0.5-5000 $cm^2$, 0.5-4000 $cm^2$, 0.5-3000 $cm^2$, 0.5-2000 $cm^2$, 1-10000 $cm^2$, 1-9000 $cm^2$, 1-8000 $cm^2$, 1-7000 $cm^2$, 1-6000 $cm^2$, 1-5000 $cm^2$, 1-4000 $cm^2$, 1-3000 $cm^2$, 1-2000 $cm^2$, 1-1500 $cm^2$, 1-1000 $cm^2$, 1-750 $cm^2$, 1-500 $cm^2$, 1-250 $cm^2$, 1-100 $cm^2$, 1-50 $cm^2$, 1-25 $cm^2$, or 1-10 $cm^2$. Other ranges are also possible. In some instances, the plasma or active electrode may have an area of about 10000 $cm^2$, 9500 $cm^2$, 9000 $cm^2$, 8500 $cm^2$, 8000 $cm^2$, 7500 $cm^2$, 7000 $cm^2$, 6500 $cm^2$, 6000 $cm^2$, 5500 $cm^2$, 5000 $cm^2$, 4500 $cm^2$, 4000 $cm^2$, 3500 $cm^2$, 3000 $cm^2$, 2500 $cm^2$, 2000 $cm^2$, 1900 $cm^2$, 1800 $cm^2$, 1700 $cm^2$, 1600 $cm^2$, 1500 $cm^2$, 1400 $cm^2$, 1300 $cm^2$, 1200 $cm^2$, 1100 $cm^2$, 1000 $cm^2$, 900 $cm^2$, 800 $cm^2$, 700 $cm^2$, 600 $cm^2$, 500 $cm^2$, 400 $cm^2$, 300 $cm^2$, 200 $cm^2$, or 100 $cm^2$.

The ground electrode may have a greatest dimension (e.g. length, width, or diameter) of about 0.1 cm, 0.5 cm, 1 cm, 5 cm, 10 cm, 15 cm, 20 cm, 25 cm, 30 cm, 35 cm, 40 cm, 45 cm, 50 cm, or greater. The ground electrode may have an area in a range of between about 0.5-10000 $cm^2$, 0.5-9000 $cm^2$, 0.5-8000 $cm^2$, 0.5-7000 $cm^2$, 0.5-6000 $cm^2$, 0.5-5000 $cm^2$, 0.5-4000 $cm^2$, 0.5-3000 $cm^2$, 0.5-2000 $cm^2$, 1-10000 $cm^2$, 1-9000 $cm^2$, 1-8000 $cm^2$, 1-7000 $cm^2$, 1-6000 $cm^2$, 1-5000 $cm^2$, 1-4000 $cm^2$, 1-3000 $cm^2$, 1-2000 $cm^2$, 1-1500 $cm^2$, 1-1000 $cm^2$, 1-750 $cm^2$, 1-500 $cm^2$, 1-250 $cm^2$, 1-100 $cm^2$, 1-50 $cm^2$, 1-25 $cm^2$, or 1-10 $cm^2$. Other ranges are also possible. In some instances, the ground electrode may have an area of about 10000 $cm^2$, 9500 $cm^2$, 9000 $cm^2$, 8500 $cm^2$, 8000 $cm^2$, 7500 $cm^2$, 7000 $cm^2$, 6500 $cm^2$, 6000 $cm^2$, 5500 $cm^2$, 5000 $cm^2$, 4500 $cm^2$, 4000 $cm^2$, 3500 $cm^2$, 3000 $cm^2$, 2500 $cm^2$, 2000 $cm^2$, 1900 $cm^2$, 1800 $cm^2$, 1700 $cm^2$, 1600 $cm^2$, 1500 $cm^2$, 1400 $cm^2$, 1300 $cm^2$, 1200 $cm^2$, 1100 $cm^2$, 1000 $cm^2$, 900 $cm^2$, 800 $cm^2$, 700 $cm^2$, 600 $cm^2$, 500 $cm^2$, 400 $cm^2$, 300 $cm^2$, 200 $cm^2$, or 100 $cm^2$.

In some instances, the plasma or active electrode and ground electrode have the same shape and same surface area.

The plasma may be supplied at any suitable power. The power may be in the range, for example, of between about 0.1 to 300 Watts, 0.1 to 275 Watts, 0.1 to 250 Watts, 0.1 to 200 Watts, 0.1 to 150 Watts, 0.1 to 100 Watts, 0.1 to 75 Watts, 0.1 to 50 Watts, 0.1 to 25 Watts, 0.1 to 10 Watts, or 0.1 to 5 Watts. Other ranges are also possible. In some instances the power may be about 10 Watts, 25 Watts, 50 Watts, 75 Watts, 100 Watts, 125 Watts, 150 Watts, 175 Watts, 200 Watts, 225 Watts, 250 Watts, 275 Watts, or 300 Watts.

The plasma may be provided at any suitable plasma power density. The plasma power density of a plasma may be defined as the energy provided by the plasma per square centimeter plasma RF electrode. In some embodiments, the plasma may be present at a plasma power density of greater than or equal to 0.1 $mW/cm^2$, greater than or equal to 0.25 $mW/cm^2$, greater than or equal to 0.5 $mW/cm^2$, greater than or equal to 0.75 $mW/cm^2$, greater than or equal to 1 $mW/cm^2$, greater than or equal to 1.5 $mW/cm^2$, greater than or equal to 2 $mW/cm^2$, greater than or equal to 5 $mW/cm^2$, greater than or equal to 7.5 $mW/cm^2$, greater than or equal to 10 $mW/cm^2$, greater than or equal to 12.5 $mW/cm^2$, greater than or equal to 15 $mW/cm^2$, greater than or equal to 20 $mW/cm^2$, greater than or equal to 30 $mW/cm^2$, greater than or equal to 35 $mW/cm^2$, greater than or equal to 40 $mW/cm^2$, greater than or equal to 45 $mW/cm^2$, or greater than or equal to 50 $mW/cm^2$. According to certain embodiments, the plasma may be present at a plasma power density of less than or equal to 50 $mW/cm^2$, less than or equal to 45 $mW/cm^2$, less than or equal to 40 $mW/cm^2$, less than or equal to 35 $mW/cm^2$, less than or equal to 30 $mW/cm^2$, less than or equal to 25 $mW/cm^2$, less than or equal to 20 $mW/cm^2$, less than or equal to 15 $mW/cm^2$, less than or equal to 12.5 $mW/cm^2$, less than or equal to 10 $mW/cm^2$, less than or equal to 7.5 $mW/cm^2$, less than or equal to 5 $mW/cm^2$, less than or equal to 2 $mW/cm^2$, less than or equal to 1.5 $mW/cm^2$, less than or equal to 1 $mW/cm^2$, less than or equal to 0.75 $mW/cm^2$, less than or equal to 0.5 $mW/cm^2$, less than or equal to 0.25 $mW/cm^2$, or less than or equal to 0.1 $mW/cm^2$. Combinations of the above-referenced ranges are also possible (e.g., greater than or equal to 0.5 $mW/cm^2$ and less than or equal to 1 $mW/cm^2$, greater than or equal to 0.5 $mW/cm^2$ and less than or equal to 2 $mW/cm^2$, greater than or equal to 0.75 $mW/cm^2$ and less than or equal to 5 $mW/cm^2$, greater than or equal to 1 $mW/cm^2$ and less than or equal to 10 $mW/cm^2$, or greater than or equal to 0.5 $mW/cm^2$ and less than or equal to 15 $mW/cm^2$). Other ranges are also possible.

The plasma may be provided at any suitable volumetric plasma power density based on the distance from the ground electrode to the active electrode and the power densities of the plasma can be as described above. The volumetric plasma power density refers to the energy provided by the plasma per volume (e.g., cubic centimeters) of the region between the active electrode and ground electrode. The corresponding volumetric power densities for the distances and plasma power density ranges described above are provided in the following table.

TABLE 1

| | | 1 cm | 3 cm | 5 cm | 8 cm | 10 cm | 15 cm | 20 cm | 25 cm | 30 cm | 50 cm |
|---|---|---|---|---|---|---|---|---|---|---|---|
| 0.5 | $mW/cm^2$ | 0.50 | 0.17 | 0.10 | 0.06 | 0.05 | 0.03 | 0.03 | 0.02 | 0.02 | 0.01 |
| 0.75 | $mW/cm^2$ | 0.75 | 0.25 | 0.15 | 0.09 | 0.08 | 0.05 | 0.04 | 0.03 | 0.03 | 0.02 |
| 1 | $mW/cm^2$ | 1.00 | 0.33 | 0.20 | 0.13 | 0.10 | 0.07 | 0.05 | 0.04 | 0.03 | 0.02 |
| 1.5 | $mW/cm^2$ | 1.50 | 0.50 | 0.30 | 0.19 | 0.15 | 0.10 | 0.08 | 0.06 | 0.05 | 0.03 |
| 2 | $mW/cm^2$ | 2.00 | 0.67 | 0.40 | 0.25 | 0.20 | 0.13 | 0.10 | 0.08 | 0.07 | 0.04 |
| 5 | $mW/cm^2$ | 5.00 | 1.67 | 1.00 | 0.63 | 0.50 | 0.33 | 0.25 | 0.20 | 0.17 | 0.10 |
| 7.5 | $mW/cm^2$ | 7.50 | 2.50 | 1.50 | 0.94 | 0.75 | 0.50 | 0.38 | 0.30 | 0.25 | 0.15 |
| 10 | $mW/cm^2$ | 10.00 | 3.33 | 2.00 | 1.25 | 1.00 | 0.67 | 0.50 | 0.40 | 0.33 | 0.20 |
| 12.5 | $mW/cm^2$ | 12.50 | 4.17 | 2.50 | 1.56 | 1.25 | 0.83 | 0.63 | 0.50 | 0.42 | 0.25 |
| 15 | $mW/cm^2$ | 15.00 | 5.00 | 3.00 | 1.88 | 1.50 | 1.00 | 0.75 | 0.60 | 0.50 | 0.30 |
| 20 | $mW/cm^2$ | 20.00 | 6.67 | 4.00 | 2.50 | 2.00 | 1.33 | 1.00 | 0.80 | 0.67 | 0.40 |
| 30 | $mW/cm^2$ | 30.00 | 10.00 | 6.00 | 3.75 | 3.00 | 2.00 | 1.50 | 1.20 | 1.00 | 0.60 |
| 35 | $mW/cm^2$ | 35.00 | 11.67 | 7.00 | 4.38 | 3.50 | 2.33 | 1.75 | 1.40 | 1.17 | 0.70 |
| 40 | $mW/cm^2$ | 40.00 | 13.33 | 8.00 | 5.00 | 4.00 | 2.67 | 2.00 | 1.60 | 1.33 | 0.80 |
| 45 | $mW/cm^2$ | 45.00 | 15.00 | 9.00 | 5.63 | 4.50 | 3.00 | 2.25 | 1.80 | 1.50 | 0.90 |
| 50 | $mW/cm^2$ | 50.00 | 16.67 | 10.00 | 6.25 | 5.00 | 3.33 | 2.50 | 2.00 | 1.67 | 1.00 |

The non-bold values shown in Table 1 are volumetric plasma power densities ($mW/cm^3$), which are obtained by dividing the power density value (left column; in bold) by the distance values from the substrate or ground electrode to the active electrode (top row; in bold). In some embodiments, the volumetric plasma power density during the plasma-enhanced chemical vapor deposition (PECVD) process is within any range based on values shown in Table 1, such as from about 0.01 $mW/cm^3$ to about 100 $mW/cm^3$, from about 0.01 $mW/cm^3$ to about 50 $mW/cm^3$, from about 0.01 $mW/cm^3$ to about 25 $mW/cm^3$, from about 0.01 $mW/cm^3$ to about 20 $mW/cm^3$, from about 0.01 $mW/cm^3$ to about 10 $mW/cm^3$, from about 0.01 $mW/cm^3$ to about 5 $mW/cm^3$, or from about 0.01 $mW/cm^3$ to about 2.5 $mW/cm^3$. In yet other embodiments the volumetric plasma power density can have a value in any suitable range, such as from about 0.001 mW/cm$^3$ to about 100 mW/cm$^3$, from about 0.001 mW/cm$^3$ to about 50 mW/cm$^3$, from about 0.001 mW/cm$^3$ to about 25 mW/cm$^3$, from about 0.001 mW/cm$^3$ to about 20 mW/cm$^3$, from about 0.001 mW/cm$^3$ to about 10 mW/cm$^3$, from about 0.001 mW/cm$^3$ to about 5 mW/cm$^3$, or from about 0.001 mW/cm$^3$ to about 2.5 mW/cm$^3$. Other ranges are also possible. Optionally, the volumetric power density during the plasma-enhanced chemical vapor deposition (PECVD) process is at least about 0.001 mW/cm$^3$, at least about 0.01 mW/cm$^3$, at least about 0.1 mW/cm$^3$, at least about 1 mW/cm$^3$, at least about 1.5 mW/cm$^3$, at least about 2.0 mW/cm$^3$, or at least about 2.5 mW/cm$^3$. The volumetric power density can be less than about 5 mW/cm$^3$, less than about 4 mW/cm$^3$, less than about 3 mW/cm$^3$, less than about 2 mW/cm$^3$, less than about 1 mW/cm$^3$, or less than about 0.01 mW/cm$^3$.

In some embodiments, volumetric plasma power density may be calculated based on an average area, which is the average of the active electrode area and the ground electrode area. The average of the active electrode area and the ground electrode area can be multiplied by the distance between the active electrode and the ground electrode to provide a volumetric value. The volumetric plasma power density based on the average area can be calculated by dividing the plasma power by the resulting volumetric value. Alternatively, volumetric plasma power density may be calculated based on the active electrode area alone. The plasma or active electrode area multiplied by the distance between the electrode and the substrate gives a volumetric value. The volumetric plasma power density based solely on active electrode area can be calculated by dividing the plasma power by the resulting volumetric value. The volumetric plasma power density, either based on average area of the active electrode area and the ground electrode area or of the active electrode area alone, can range from about 0.01 mW/cm$^3$ to about 100 mW/cm$^3$, from about 0.01 mW/cm$^3$ to about 50 mW/cm$^3$, from about 0.01 mW/cm$^3$ to about 25 mW/cm$^3$, from about 0.01 mW/cm$^3$ to about 20 mW/cm$^3$, from about 0.01 mW/cm$^3$ to about 10 mW/cm$^3$, or from about 0.01 mW/cm$^3$ to about 5 mW/cm$^3$, or from about 0.3 to about 2.0 mW/cm$^3$. In yet other embodiments, the volumetric plasma power density, either based on average area of the active electrode area and the ground electrode area or of the active electrode area alone, can range from about 0.001 mW/cm$^3$ to about 100 mW/cm$^3$, from about 0.001 mW/cm$^3$ to about 50 mW/cm$^3$, from about 0.001 mW/cm$^3$ to about 25 mW/cm$^3$, from about 0.001 mW/cm$^3$ to about 20 mW/cm$^3$, from about 0.001 mW/cm$^3$ to about 10 mW/cm$^3$, from about 0.001 mW/cm$^3$ to about 5 mW/cm$^3$, from about 0.001 mW/cm$^3$ to about 2.5 mW/cm$^3$, or from about 0.3 to about 2.0 mW/cm$^3$. Other ranges are also possible. In some embodiments, the active electrode and ground electrode areas are equal, and the volumetric plasma power density, whether based on average area or plasma or active electrode area, is the same.

In accordance with some embodiments, polymerization may occur in a reaction chamber. In some embodiments, the reaction chamber may further comprise a reaction volume where polymerization occurs. According to certain embodiments, the plasma may be substantially uniform throughout a reaction volume within the reaction chamber. Plasma uniformity may be characterized by the ratio of the standard deviation of the power density over the reaction volume to the average power density over the reaction volume. In some embodiments, the ratio of the standard deviation of the power density over the chamber volume to the average power density over the chamber volume is less than or equal to 25%, less than or equal to 20%, less than or equal to 15%, less than or equal to 10%, or less than or equal to 5%. Other ranges are also possible.

In some embodiments, a high plasma uniformity may be achieved by incorporating certain design elements into the reaction chamber. For example, in certain embodiments a reaction chamber may comprise an electrode(s), such as an active electrode that acts as a plasma source and provides the plasma during deposition of a polymer and a ground electrode. In some embodiments, there may be coupling near the center of the electrode. According to certain embodiments, a reaction chamber may comprise an inlet power source. In some embodiments, the inlet power source may be shielded. Other design features which may improve plasma uniformity in a reaction chamber may also be incorporated.

According to certain embodiments, the one or more monomer(s), initiator(s), and/or inert gas may flow into the reaction chamber prior to polymerization. In some embodiments, these species will then either flow out of the reaction chamber or polymerize to form a polymer on a substrate. The residence time of a species may be defined as the total amount of time that that species spends in the reaction chamber prior to either flowing out or undergoing polymerization. The residence times for the monomer(s), initiator (s), and inert gas(es) may be any suitable value. In some embodiments, each of the one or more monomer(s), initiator (s) and inert gas(es) may independently have a residence time of greater than or equal to 5 seconds, greater than or equal to 10 seconds, greater than or equal to 15 seconds, greater than or equal to 30 seconds, greater than or equal to 45 seconds, greater than or equal to 60 seconds, greater than or equal to 90 seconds, greater than or equal to 120 seconds, or greater than or equal to 180 seconds. According to certain embodiments, each of the one or more monomer(s), initiator (s) and inert gas(es) has a residence time of less than or equal to 300 seconds, less than or equal to 180 seconds, less than or equal to 120 seconds, less than or equal to 90 seconds, less than or equal to 60 seconds, less than or equal to 45 seconds, less than or equal to 30 seconds, less than or equal to 15 seconds, or less than or equal to 10 seconds. Combinations of the above-referenced ranges are also possible (e.g., greater than or equal to 15 seconds and less than or equal to 90 seconds). Other ranges are also possible. In some embodiments, the residence time of all of the species is substantially similar. In accordance with some embodiments, a method for synthesizing a polymer may comprise one or more deposition cycles.

According to certain embodiments, a coating deposition may comprise forming a polymer on a substrate at any suitable rate. In some embodiments, the rate may be greater than or equal to 0.01 nm/min, greater than or equal to 0.025 nm/min, greater than or equal to 0.05 nm/min, greater than or equal to 0.1 nm/min, greater than or equal to 0.25 nm/min, greater than or equal to 0.5 nm/min, greater than or equal to 1 nm/min, greater than or equal to 2.5 nm/min, greater than or equal to 5 nm/min, greater than or equal to 10 nm/min, greater than or equal to 25 nm/min, or greater than or equal to 50 nm/min. In accordance with certain embodiments, the rate may be less than or equal to 100 nm/min, less than or equal to 50 nm/min, less than or equal to 25 nm/min, less than or equal to 10 nm/min, less than or equal to 5 nm/min, less than or equal to 2.5 nm/min, less than or equal to 1 nm/min, less than or equal to 0.5 nm/min, less than or equal to 0.25 nm/min, less than or equal to 0.1 nm/min, less than or equal to 0.05 nm/min, or less than or equal to 0.025 nm/min Combinations of the above-referenced ranges are also possible (e.g., greater than or equal to 0.025 nm/min and less than or equal to 1 nm/min). Other ranges are also possible.

According to some embodiments, the polymer may be formed on at least a portion of a substrate (e.g., a portion of a substrate surface), or on substantially all of the substrate (e.g., substantially all of the substrate surface). Any suitable substrate may be used. In some embodiments, the substrate or at least a portion of the substrate may be conductive. The substrate may comprise a single material and/or a plurality of materials. The substrate may comprise one or more electronic components and/or may be functional device (e.g., an RF device). For example, the substrate may be a portion of a functional device, for example, a CMOS substrate, a printed circuit board, a flexible circuit, an electronic circuit, and/or an electronic chip. Functional devices are described in more detail herein. The substrate may be transparent, semi-transparent, semi-opaque, and/or opaque. The substrate may be solid, semi-porous, and/or porous.

In certain embodiments, the substrate or at least a portion of the substrate comprises a conductive material (e.g., a metal). Non-limiting examples of substantially conductive materials the substrate may comprise includes indium tin oxide (ITO), fluorine tin oxide (FTO), antimony-doped tin oxide (ATO), aluminum-doped zinc oxide (AZO), glassy carbon, carbon mesh, metals, metal alloys, lithium-containing compounds, metal oxides (e.g., platinum oxide, nickel oxide, zinc oxide, tin oxide, vanadium oxide, zinc-tin oxide, indium oxide, indium-zinc oxide), graphite, zeolites, and the like. Non-limiting examples of suitable metals the substrate may comprise (including metals comprised in metal alloys and metal oxides) include gold, copper, silver, platinum, ruthenium, rhodium, osmium, iridium, nickel, cadmium, tin, lithium, chromium, calcium, titanium, aluminum, cobalt, zinc, vanadium, nickel, palladium, or the like, and combinations thereof. In some embodiments, at least a portion of the substrate comprises a non-conductive material, for example, an inorganic material, (e.g., quartz, glass, etc.) or a polymeric material (e.g., polyethylene terephthalate, polyethylene naphthalate, polycarbonate, polystyrene, polypropylene, etc.).

In some embodiments, the substrate comprises an alloy, such as a solder or a solder flux. In some embodiments, the substrate comprises an comprises a ceramic. In some embodiments, the ceramic comprises a ceramic cation and a ceramic anion. Non-limiting examples of suitable ceramic cations include aluminum, silicon, indium and gallium. Non-limiting examples of suitable ceramic anions include carbide, arsenide, antimonide, phosphide, sulfide, and nitride ions.

In some embodiments, the substrate comprises a semiconductor, for example, silicon, germanium, an alloy comprising at least one of silicon and germanium, an alloy comprising silicon and germanium, and/or an antimonide-based compound semiconductor. In certain embodiments, the substrate may comprise one or more of aluminum nitride, silicon carbide, indium phosphide, gallium sulfide, gallium arsenide, and gallium nitride. In some embodiments, the semiconductor may comprise at least one semiconductor cation and at least one semiconductor anion. Non-limiting examples of semiconductor cations include aluminum, silicon, indium and gallium. Non-limiting examples of semiconductor anions include carbide, arsenide, antimonide, phosphide, sulfide, and nitride ions. Those of ordinary skill in the art will be aware of other semiconductor materials.

In some embodiments, the polymer is formed on substantially all of or all of the substrate surface. In some embodiments, the polymer substantially encompasses or covers substantially all of the substrate (e.g., greater than about 99%, about 99.5%, about 99.8%, about 99.9%, about 99.99%, or 100% of the substrate is encompasses by the polymer). In such embodiments, as described herein, the polymer films may be capable of protecting the substrate (e.g., from environmental conditions such as high temperature and/or humidity). In other embodiments, a portion of the substrate is covered. In some embodiments, the portion of the substrate susceptible to environmental conditions (e.g., temperature and/or humidity) is covered by the polymer.

The substrate may be of any size or shape. Non-limiting examples of shapes include sheets, cubes, cylinders, hollow tubes, spheres, and the like. The substrate may be of any suitable size. The methods described herein are particularly amenable to forming a polymer on any shape and/or size of substrate. In some cases, the maximum dimension of the substrate in one dimension may be at least about 1 mm, at least about 1 cm, at least about 5 cm, at least about 10 cm, at least about 1 m, at least about 2 m, or greater. In some cases, the minimum dimension of the substrate in one dimension may be less than about 50 cm, less than about 10 cm, less than about 5 cm, less than about 1 cm, less than about 10 mm, less than about 1 mm, less than about 1 um, less than about 100 nm, less than about 10 nm, less than about 1 nm, or less. The substrate may or may not be substantially planar. For example, the substrate may comprise ripples, waves, dendrimers, spheres (e.g., nanospheres), rods (e.g., nanorods), a powder, a precipitate, a plurality of particles, and the like.

In certain embodiments, the substrate may undergo one or more preparation steps prior to serving as a substrate on which the polymer will form. Several possible preparation steps are described below. For example, in some embodiments, the substrate may be cleaned by exposing the substrate to a fluid and then soaking the substrate in the fluid, rinsing the substrate with the fluid, and/or sonicating the substrate in the presence of the fluid prior to the reaction in some embodiments. Non-limiting examples of suitable fluids for such processes include organic solvents, water, and/or solutions comprising an organic or aqueous solvent and a surfactant.

In some embodiments, the substrate may be exposed to an elevated temperature and/or a reduced pressure in order to remove volatile contaminants. Suitable temperatures include temperatures between 20° C. and 300° C. Suitable pressures include pressures between 0.1 mTorr and 1 atm.

According to certain embodiments, the substrate may undergo a plasma cleaning step prior to the reaction. Other preparation steps are also possible.

In some embodiments, one or more adhesion-promoting linkers may be applied to the substrate. Non-limiting examples of such linkers include silane-containing compounds, organophosphate-containing compounds, and thiol-containing compounds.

According to certain embodiments, polymers formed by the methods described herein may be formed as films on the surface of a substrate. These films may have any average suitable thickness. In some embodiments, films formed by the methods described herein may have an average thickness of greater than or equal to 25 nm, greater than or equal to 50 nm, greater than or equal to 75 nm, greater than or equal to 100 nm, greater than or equal to 250 nm, greater than or equal to 500 nm, greater than or equal to 750 nm, greater than or equal to 1 um, greater than or equal to 2.5 um, greater than or equal to 5 um, greater than or equal to 7.5 um, greater than or equal to 10 um, greater than or equal to 25 um, or greater than or equal to 50 um. According to certain embodiments, films formed by the methods described herein may have an average thickness of less than or equal to 100 um, less than or equal to 50 um, less than or equal to 25 um, less than or equal to 10 um, less than or equal to 7.5 um, less than or equal to 5 um, less than or equal to 2.5 um, less than or equal to 1 um, less than or equal to 750 nm, less than or equal to 500 nm, less than or equal to 250 nm, less than or equal to 100 nm, less than or equal to 75 nm, or less than or equal to 50 nm. Combinations of the above-referenced ranges are also possible (e.g., greater than or equal to 50 nm and less than or equal to 10 um, greater than or equal to 100 nm and less than or equal to 10 um, or greater than or equal to 100 nm and less than or equal to 1 um). Other ranges are also possible. It should also be noted that while much of the discussion herein focuses on polymers being deposited as films and/or thin films, this is by no means limiting and the polymer may be in other forms, e.g., as a thicker film, as a coating, or as a bulk material.

In some cases, the thickness of film may be of substantially the same throughout the material. In other cases, the thickness of the film may vary throughout the material (e.g., a film does not necessarily have uniform thickness). The thickness of the film may be determined by determining the thickness of the film at a plurality of areas (e.g., at least 2, at least 4, at least 6, at least 10, at least 20, at least 40, at least 50, at least 100, or more areas) and calculating the average thickness. Where thickness of a film is determined via probing at a plurality of areas, the areas may be selected so as not to specifically represent areas of more or less polymer present based upon a pattern. In some embodiments, the difference in thickness between the thickest part of the film and the thinnest part of the film may be relatively small. For instance, the difference in thickness between the thickest part of the film and the thinnest part of the film may be less than or equal to 25% of the average film thickness, less than or equal to 10% of the average film thickness, less than or equal to 5% of the average film thickness, less than or equal to 2% of the average film thickness, or less than or equal to 1% of the average film thickness.

One of ordinary skill in the art would be aware of methods for determining the thickness of a film. In one approach, a witness coupon (i.e., a substrate comprising a smooth surface such as a silicon wafer or a glass wafer) is placed in the deposition chamber during substrate coating. Subsequent to deposition, a scratch is made on the witness coupon down to the bare substrate and the thickness of the coating measured using a contact profilometer.

In some embodiments, films formed by the methods described herein may comprise one or more layers. In some embodiments, following formation of the polymer film, a different material may be deposited on the film (e.g., a fluoropolymer).

According to certain embodiments, additional processing steps may be performed after plasma deposition of the film. For example, in some embodiments the film may be subjected to a heat treatment. In some embodiments, the polymer may be subjected to a temperature of greater than or equal to 50° C., greater than or equal to 60° C., greater than or equal to 70° C., greater than or equal to 80° C., greater than or equal to 90° C., greater than or equal to 100° C., greater than or equal to 125° C., greater than or equal to 150° C., greater than or equal to 175° C., greater than or equal to 200° C., greater than or equal to 225° C., greater than or equal to 250° C., greater than or equal to 275° C., greater than or equal to 300° C., or greater than or equal to 325° C. According to certain embodiments, the polymer may be subjected to a temperature of less than or equal to 350° C., less than or equal to 325° C., less than or equal to 300° C., less than or equal to 275° C., less than or equal to 250° C., less than or equal to 225° C., less than or equal to 200° C., less than or equal to 175° C., less than or equal to 150° C., less than or equal to 125° C., less than or equal to 100° C., less than or equal to 90° C., less than or equal to 80° C., less than or equal to 70° C., or less than or equal to 60° C. Combinations of the above-referenced ranges are also possible (e.g., greater than or equal to 225° C. and less than or equal to 275° C.). Other ranges are also possible.

In some embodiments, the film may be subjected to a heat treatment for a certain amount of time. For example, in certain embodiments the polymer may be subjected to a heat treatment for greater than or equal to 30 minutes, greater than or equal to 1 hour, greater than or equal to 2 hours, greater than or equal to 5 hours, greater than or equal to 10 hours, greater than or equal to 15 hours, greater than or equal to 20 hours, greater than or equal to 24 hours, or greater than or equal to 30 hours. In some embodiments, the film may be subjected to a heat treatment for less than or equal to 48 hours, less than or equal to 30 hours, less than or equal to 24 hours, less than or equal to 20 hours, less than or equal to 15 hours, less than or equal to 10 hours, less than or equal to 5 hours, less than or equal to 2 hours, or less than or equal to 1 hour. Combinations of the above-referenced ranges are also possible (e.g., greater than or equal to 1 hour and less than or equal to 24 hours). Other ranges are also possible.

The film may be subjected to a heat treatment while under any suitable ambient environment. In some embodiments, the heat treatment may be applied while the film is under a reduced pressure environment. For instance, in certain embodiments the film may be at a pressure of less than or equal to 760 Torr, less than or equal to 500 Torr, less than or equal to 250 Torr, less than or equal to 100 Torr, less than or equal to 50 Torr, less than or equal to 25 Torr, less than or equal to 10 Torr, less than or equal to 5 Torr, less than or equal to 2.5 Torr, less than or equal to 1 Torr, less than or equal to 0.5 Torr, less than or equal to 0.25 Torr, less than or equal to 0.1 Torr, less than or equal to 0.05 Torr, less than or equal to 0.025 Torr, or less than or equal to 0.01 Torr. In some embodiments, the film may be at a pressure of greater than or equal to 0.005 Torr, greater than or equal to 0.01 Torr, greater than or equal to 0.025 Torr, greater than or equal to 0.05 Torr, greater than or equal to 0.1 Torr, greater than or equal to 0.25 Torr, greater than or equal to 0.5 Torr, greater than or equal to 1 Torr, greater than or equal to 2.5 Torr, greater than or equal to 5 Torr, greater than or equal to 10 Torr, greater than or equal to 25 Torr, greater than or equal to 50 Torr, greater than or equal to 100 Torr, greater than or equal to 250 Torr, or greater than or equal to 500 Torr. Combinations of the above-referenced ranges are also possible (e.g., greater than or equal to 0.01 Torr and less than or equal to 0.1 Torr). Other ranges are also possible. In certain embodiments, the film may be subjected to a heat treatment at 80° C. while being in an environment where the pressure of less than or equal to 0.01 Torr.

In some embodiments, the film may be subjected to a heat treatment while under a gaseous atmosphere. The gaseous atmosphere may comprise any suitable gas or gases. According to certain embodiments, the gaseous atmosphere may be an inert atmosphere, or may comprise one or more of nitrogen, argon, and helium. In some embodiments, the gaseous atmosphere may comprise air. In accordance with some embodiments, the film may be subjected to a heat treatment at 250° C. while in an inert environment. In certain embodiments, the film may be subjected to a heat treatment at 250° C. while being exposed to air. According to some embodiments, the film may be subjected to a heat treatment at 250° C. while under a reduced pressure environment. Other combinations of heat treatment temperature and gaseous environment are also possible.

The methods described herein may be used to synthesize films with certain beneficial physical properties. For example, in some embodiments the methods described herein may be used to synthesize films which comprise a low number of defects, such as pinholes and/or cracks. According to certain embodiments, the films may be substantially defect free.

The number of defects may be determined by any suitable means. In some embodiments, the number of defects in a film may be determined by exposing the film to a 0.1% sodium dodecyl sulfate solution in deionized water while causing the film to undergo a voltage sweep between 0 and 25 V. Then, images may be collected of the film at each voltage and image analysis may be used to quantify the size and number of defects. Other methods for determining the number of defects are also possible. In some embodiments, the films exhibit substantially no defects at the voltage of interest for the application.

In some embodiments the methods described herein may be used to synthesize films which comprise a high water vapor permeability. In accordance with certain embodiments, films may comprise a water vapor permeability of greater than or equal to 250 $g/m^2/day$, greater than or equal to 500 $g/m^2/day$, greater than or equal to 750 $g/m^2/day$, greater than or equal to 1000 $g/m^2/day$, greater than or equal to 1250 $g/m^2/day$, greater than or equal to 1500 $g/m^2/day$, greater than or equal to 1750 $g/m^2/day$, greater than or equal to 2000 $g/m^2/day$, or greater than or equal to 2250 $g/m^2/day$. According to some embodiments, films may comprise a water vapor permeability of less than or equal to 2500 $g/m^2/day$, less than or equal to 2250 $g/m^2/day$, less than or equal to 200 $g/m^2/day$, less than or equal to 1750 $g/m^2/day$, less than or equal to 1500 $g/m^2/day$, less than or equal to 1250 $g/m^2/day$, less than or equal to 1000 $g/m^2/day$, less than or equal to 750 $g/m^2/day$, or less than or equal to 500 $g/m^2/day$. Combinations of the above-referenced ranges are also possible (e.g., greater than or equal to 250 $g/m^2/day$ and less than or equal to 2250 $g/m^2/day$, greater than or equal to 500 $g/m^2/day$ and less than or equal to 2000 $g/m^2/day$, or greater than or equal to 1000 $g/m^2/day$ and less than or equal to 1500 $g/m^2/day$). Other ranges are also possible.

One of ordinary skill in the art would be familiar with methods for determining water vapor permeability. In some embodiments, water vapor permeability may be assessed using ASTM E398. This standard measures the rate of transfer of water vapor through a flexible barrier material with at least one hydrophobic surface. The barrier material is mounted between a first chamber with a known relative humidity and a second chamber initially containing dry air. The humidity in the second chamber is measured as a function of time in order to determine the rate of water vapor transmission. According to certain embodiments, the films may be capable of passing one or more standard tests which can be used to determine the ability of coatings to protect a substrate from high temperature and/or humidity environmental conditions. In general, unless otherwise specified, a film that passes a standard test has properties in accordance with those described herein for films (e.g., siloxane ring content, vinyl group content, water vapor permeability, freedom from defects, dielectric constant, dielectric breakdown voltage, adhesion strength, and the like) after undergoing the testing procedure. In some embodiments, the films may pass the standard test and have a relatively small change in the properties described herein (e.g., siloxane ring content, vinyl group content, water vapor permeability, freedom from defects, dielectric constant, dielectric breakdown voltage, adhesion strength, and the like). For example, one or more of the properties described herein may change by less than 25%, less than 10%, less than 5%, less than 2%, or less than 1% after undergoing a testing procedure described herein.

In some embodiments, the films may be capable of passing the Military Specification for Insulating Compound, Electrical (for Coating Printed Circuit Assemblies), published as MIL-I-46058C on Jul. 7, 1972 and incorporated herein by reference in its entirety and for all purposes. This specification describes properties that a film must have in order to be suitable for use as a coating on printed circuit assemblies by the Department of Defense. As described therein, the film is formed on a substrate, and then subject to various testing conditions to determine its properties. Relevant tests and acceptable properties are described in further detail below. In some embodiments, the film may have some or all of the properties described therein.

In some embodiments, films that are suitable under MIL-I-46058C are free from deleterious substances, are chemically compatible with the materials used to form the printed circuit assembly, do not cause deterioration of any materials used to form the printed circuit assembly, and do not corrode any metals being coated.

In some embodiments, films that are suitable under MIL-I-46058C are smooth, homogeneous, transparent, and unpigmented. The films may be free from bubbles, pinholes, whitish spots, blistering, wrinkling, cracking, and peeling. In some embodiments, the films do not mask or obliterate any identification markings that may be present, and/or does not cause greater discoloration of the substrate than would be caused by conditioning of an uncoated substrate. These properties may be determined by inspecting the films under 10× magnification.

In some embodiments, films that are suitable under MIL-I-46058C may be resistant to fungus. The films may show no fungal growth when assessed by ASTM G-21, which comprises placing three samples of glass coated with the film into petri dishes filled with minimal salts agar, spraying fungal spores in a minimal salt solution onto the samples, sealing the samples, and incubating them for 28 days. Photographs are taken of each sample at regular intervals and compared to photographs taken of both a positive control (uncoated substrate) and a negative control (solid agar medium that was unexposed to the spores). The fungal spores include spores from the *Penicillium, Aspergillus, Chaetomium, Trichoderma, Aureobasidium,*

In some embodiments, films that are suitable under MIL-I-46058C may have an insulation resistance of greater than or equal to $1.5*10^{12}$ ohms and less than or equal to $10^{14}$ ohms, or greater than or equal to $2.5*10^{12}$ ohms and less than or equal to $10^{14}$ ohms. The insulation resistance may be measured using the procedure described in MIL-STD-202 for method 302, test condition B. This test condition comprises coating the film on a megohm bridge, applying 500+/−10% V to the megohm bridge for one minute, and then measuring the insulation resistance across the film.

In some embodiments, films that are suitable under MIL-I-46058C may show no flashover, sparkover, breakdown, or leakage rate in excess of 10 microamperes when tested using the procedure described in MIL-STD-202 for method 301. This procedure comprises applying 1500 V, alternating current, root mean square, at 60 Hz between two mutually insulated portions of the sample for 60 seconds.

In some embodiments, films that are suitable under MIL-I-46058C may have favorable properties after being subject to thermal shock as described in MIL-STD-202, method 107. The films may be subject to the following temperatures in sequence 50 times: −70−−65° C., 20-35° C., 200-205° C., and 20-35° C. for a time as specified in MIL-STD-202, method 107 (e.g., 15 minutes for samples weighing less than or equal to 1 ounce; 30 minutes for greater than 1 ounce and less than or equal to 0.3 pounds; 1 hour for samples weighing greater than 0.3 pounds and less than or equal to 3 pounds; 2 hours for samples weighing greater than 3 pounds and less than or equal to 30 pounds; 4 hours for samples weighing greater than 30 pounds and less than or equal to 300 pounds; 8 hours for samples weighing greater than 300 pounds). Then, the films may be held at 23-27° C. and 45-55% relative humidity for 35 hours. After this test, the films may show suitable properties after being inspected using microscopy and subject to MIL-STD-202 method 301, as described above.

In some embodiments, films that are suitable under MIL-I-46058C may be capable of undergoing a modification of the procedure described in MIL-STD-202 for method 106 and then showing an insulation resistance of greater than or equal to $1.5*10^{12}$ ohms and less than or equal to $10^{14}$ ohms, or greater than or equal to $2.5*10^{12}$ ohms and less than or equal to $10^{14}$ ohms, suitable properties after being inspected using microscopy, and may show no flashover, sparkover, breakdown, or leakage rate in excess of 10 microamperes when tested using the procedure described in MIL-STD-202 for method 301. The modified method comprises exposing the film to a cycle with steps comprising defined humidities ranging from 80%-100% relative humidity and temperatures ranging from 25° C. to 65° C. Then, the film may be held at 25+/−2° C. and 50+/−5% relative humidity for 24 hours.

According to certain embodiments, the films may be capable of meeting the requirements detailed in the publication "IPC-CC-830B with Amendment 1 Qualification and Performance of Electrical Insulating Compound for Printed Wiring Assemblies", published October 2008 and incorporated herein by reference in its entirety and for all purposes. This publication details performance metrics for coatings. In some embodiments, the films may have some or all of the properties described therein.

In some embodiments, the films may meet the requirements detailed in the publication "IPC-CC-830B with Amendment 1 Qualification and Performance of Electrical Insulating Compound for Printed Wiring Assemblies" with respect to appearance. The films may show no deleterious substances, bubbles, pinholes, whitish spots, blistering, cracking, peeling, crazing, mealing, evidence of reversion, or evidence of corrosion. The films may be smooth, homogeneous, transparent or translucent, and tack-free. The films may be inspected to determine these properties at 10× magnification.

In some embodiments, the films may meet the requirements detailed in the publication "IPC-CC-830B with Amendment 1 Qualification and Performance of Electrical Insulating Compound for Printed Wiring Assemblies" with respect to fungus resistance. The films may not contribute to or be attacked by biological growth after being inoculated with spores, incubated at 28° C.-30° C. at 85% relative humidity for 28 days, and then assessed to determine fungal growth. The fungal spores may include spores from *Aspergillus niger, Chaetomium globosum, Gliocadium virans, Aureobasidium pullulans*, and *Penicillium funiculosum*.

In some embodiments, the films may meet the requirements detailed in the publication "IPC-CC-830B with Amendment 1 Qualification and Performance of Electrical Insulating Compound for Printed Wiring Assemblies" with respect to the dielectric withstanding voltage. The films may not show flashover, sparkover, breakdown, or a leakage current in excess of 10 microamperes after being subject to IPC-TM-650, Test Method 2.5.7.1. This test comprises subjecting the films to a voltage of 1500 VAC at 50-60 Hz for one minute.

In some embodiments, the films may meet the requirements detailed in the publication "IPC-CC-830B with Amendment 1 Qualification and Performance of Electrical Insulating Compound for Printed Wiring Assemblies" with respect to moisture and insulation resistance. Meeting these requirements may comprise having certain desirable properties after testing the films in accordance with IPC-TM-650, Test Method 2.6.3.4. This test method comprises forming the film on a substrate comprising a test pattern, preconditioning the film at 50+/−2° C. for 24 hours, cooling the film to room temperature, applying a 50 VDC polarizing bias to the test pattern, and exposing the film to 20 cycles of temperature and humidity. At the conclusion of the test, the film may be held at 25+/−2° C. and 50+/−5% relative humidity for 24 hours. The temperature and humidity cycles comprise raising the temperature from 25° C. to 65° C. over a span of 1.75+/−0.75 hours, maintaining the temperature at 65° C. for 3-3.5 hours, and then lowering the temperature to 25° C. over 1.75+/−0.5 hours. The resistance of the film may be measured after the first, fourth, seventh, and tenth cycles between the second and third hour of the high temperature step. The resistance of the film may also be measured at the conclusion of the test. In some embodiments, the film may show an insulation resistance of at least 5000 megohms at the conclusion of the test, may have a dielectric withstanding voltage as described above at the conclusion of the test, and may meet the appearance requirements as described above at the conclusion of the test.

In some embodiments, the films may meet the requirements detailed in the publication "IPC-CC-830B with Amendment 1 Qualification and Performance of Electrical Insulating Compound for Printed Wiring Assemblies" with respect to thermal shock. The films may show an acceptable dielectric withstanding voltage and an appearance after being subject to IPC-TM-650, Test Method 2.6.7.1. This test method comprises exposing the films to 100 temperature cycles where the films are cycled from −65° C. to 125° C., and then holding the films at 25+/−5° C. for 24 hours.

In some embodiments, the films may meet the requirements detailed in the publication "IPC-CC-830B with Amendment 1 Qualification and Performance of Electrical Insulating Compound for Printed Wiring Assemblies" with respect to hydrolytic stability. The films may meet the appearance standards described above and may be tack-free after being subject to IPC-TM-650, Test Method 2.6.11.1. This test method comprises placing the films on a ceramic plate in a desiccator comprising a saturated solution of deionized water and potassium sulfate at 85+/−2° C., closing the desiccator, sealing the desiccator with high temperature silicone grease, and placing the sealed desiccator in an oven held at 85+/−2° C. for 120 days. After this treatment, the films may be held at 25° C. and 50% relative humidity for 7 days. The films may also be brought to 25° C. and 50% relative humidity for two hours and then inspected on the $28^{th}$, $56^{th}$, and $84^{th}$ days.

In accordance with certain embodiments, the films may be capable of passing one or more of the tests detailed in methods 507.5 and 509.5 in the Department of Defense Test Method Standard Environmental Engineering Considerations and Laboratory Tests, published as MIL-STD-810G on Oct. 31, 2008 and incorporated herein by reference in its entirety and for all purposes.

Method 507.5 in Department of Defense Test Method Standard Environmental Engineering Considerations and Laboratory Tests, published as MIL-STD-810G on Oct. 31, 2008 describes a procedure for determining the resistance of protective coatings on materials to warm, humid atmospheres. In some embodiments, the films are capable of undergoing this procedure and having properties (e.g., siloxane ring content, vinyl group content, water vapor permeability, freedom from defects, dielectric constant, dielectric breakdown voltage, adhesion strength, and the like) that fall within the parameters described herein after the test has concluded. In some embodiments, the films are capable of undergoing this procedure and exhibiting a change in the dielectric breakdown voltage and/or dielectric constant of less than 25%, less than 10%, less than 5%, less than 2%, or less than 1%.

The aggravated cycle for method 507.5 in MIL-STD-810G on Oct. 31, 2008 comprises placing the coated article in a chamber and exposing it to a temperature of 23+/−2° C. and a humidity of 50+/−5% relative humidity for a period of at least 24 hours. Then, the temperature of the chamber is raised to 30° C. and the relative humidity of the chamber is raised to 95%. Next, the coated article is caused to undergo 10 cycles, where each cycle comprises raising the temperature from 30° C. to 60° C. over a period of 2 hours, holding the temperature at 60° C. for 6 hours, cooling the temperature to 30° C. over 8 hours, and holding the temperature at 30° C. for 8 hours. At the conclusion of the 10 cycles, the temperature of the chamber is returned to 30+/−2° C. and the humidity of the chamber is returned to 50+/−5% relative humidity. The coated article is maintained under these conditions until the coated article has reached temperature stabilization.

Method 509.5 5 in the Department of Defense Test Method Standard Environmental Engineering Considerations and Laboratory Tests, published as MIL-STD-810G on Oct. 31, 2008 describes a procedure for assessing the effectiveness of protective coatings on materials when exposed to salt. In some embodiments, the films are capable of undergoing this procedure and having properties (e.g., siloxane ring content, vinyl group content, water vapor permeability, freedom from defects, dielectric constant, dielectric breakdown voltage, adhesion strength, and the like) that fall within the parameters described herein after the test has concluded. In some embodiments, the films are capable of undergoing this procedure and exhibiting a change in the dielectric breakdown voltage and/or dielectric constant of less than 25%, less than 10%, less than 5%, less than 2%, or less than 1%.

Method 509.5 5 in MIL-STD-810G on Oct. 31, 2008 comprises placing the coated article in a chamber, adjusting the temperature to 35° C., and conditioning the coated article at this temperature for at least two hours. Then, a 5% solution of sodium chloride in water is continuously atomized into the test chamber for 24 hours. The salt fog fallout rate and the pH of the fallout solution are measured every 24 hours, and the fallout is kept between 1 and 3 mL/80 cm$^2$/hour. The coated article is then dried at standard ambient temperature and a relative humidity of less than 50 percent for 24 hours, after which the coated article is again exposed to the atomized salt solution for 24 hours and then dried for 24 hours once again. Then, the coated article is photographed, rinsed with running water under standard ambient conditions, and then examined for evidence of corrosion. The extent of salt deposits is noted, the article is tested for electrical malfunction, and any corrosion observed is assessed to determine its immediate and potential long term effects on the functionality and structural integrity of the article.

In some embodiments, the films may be capable of passing one or more tests published by JEDEC. As used herein, a film that passes a test published by JEDEC is capable of undergoing the JEDEC procedure and, at the conclusion of the procedure, having properties (e.g., siloxane ring content, vinyl group content, water vapor permeability, freedom from defects, dielectric constant, dielectric breakdown voltage, adhesion strength, and the like) that fall within the parameters described herein. In some embodiments, the films are capable of undergoing one or more JEDEC procedures and exhibiting a change in the dielectric breakdown voltage and/or dielectric constant of less than 25%, less than 10%, less than 5%, less than 2%, or less than 1%.

For example, the films may be capable of passing the JEDEC Standard No. 22-A101C: Steady State Temperature Humidity Bias Life Test, published March 2009 and incorporated herein by reference in its entirety and for all purposes. JEDEC Standard No. 22-A101C: Steady State Temperature Humidity Bias Life Test comprises exposing the films to a stress condition comprising a temperature of 85+/−2° C. and a relative humidity of 85+/−5% for 976-1168 hours under 10 V dc bias conditions. Then, the sample is cooled to ambient and held there for up to 48 hours. Electrical tests may then be performed on the films. Optionally, the devices may be returned to the stress condition within 96 hours of cooling.

According to certain embodiments, the films may be capable of passing the JEDEC Standard No. 22-A110D: Highly Accelerated Temperature and Humidity Stress Test (HAST), published January 2009 incorporated herein by reference in its entirety and for all purposes. JEDEC Standard No. 22-A110D comprises exposing the films to a stress condition of 130+/−2° C. and 85+/−5% relative humidity for 96-98 hours under 10 V dc bias conditions. Then, the sample is cooled to ambient and held there for up to 48 hours. Electrical tests may then be performed on the films. Optionally, the devices may be returned to the stress condition within 96 hours of cooling.

In some embodiments, the films may be capable of passing the JEDEC Standard No. 22-A100D: Cycled Temperature-Humidity-Bias Life Test, published July 2013 and incorporated herein by reference in its entirety and for all purposes. This test comprises exposing the films to an experimental profile comprising an increase in temperature from 30° C. to 65° C. at 80%-98% relative humidity over 2-4 hours, a constant temperature of 65° C. at 90%-98% relative humidity for 4-8 hours, and a decrease in temperature from 65° C. to 30° C. at 80%-90% relative humidity over the course of 2-4 hours. This cycle is repeated over a duration of time between 1084-1172 hours, while the film is under 10 V dc bias conditions. The films are then cooled to ambient and held there for up to 48 hours. Electrical tests may then be performed on the films. Optionally, the devices may be returned to the stress condition within 96 hours of cooling.

In accordance with certain embodiments, the films may be capable of passing a test conducted according to ASTM B117-16 Standard Practice for Operating Salt Spray (Fog Apparatus), published March 2016 and incorporated herein by reference in its entirety and for all purposes. In some embodiments, the films may be capable of undergoing the procedure outlined in ASTM B117-16 and, at the conclusion of the procedure, having properties (e.g., siloxane ring content, vinyl group content, water vapor permeability, freedom from defects, dielectric constant, dielectric breakdown voltage, adhesion strength, and the like) that fall within the parameters described herein. In some embodiments, the films are capable of undergoing the procedure outlined in ASTM B117-16 and exhibiting a change in the dielectric breakdown voltage and/or dielectric constant of less than 25%, less than 10%, less than 5%, less than 2%, or less than 1%. Performing the ASTM B117-16 test comprises placing the films in a chamber held at 35+/−2° C. and exposing the films to a fog of a salt solution comprising 5 wt % sodium chloride at a pH between 6.5 and 7.2 for 24 hours twice.

In some embodiments, the films' ability to pass one or more standard tests may be substantially unaffected by undergoing a stress test and/or undergoing elongation. In some embodiments, a percent elongation may be defined as the difference between the elongated length and the initial length divided by the initial length. According to certain embodiments, the films may retain their ability to pass one or more standardized tests after undergoing an elongation of greater than or equal to 1%, greater than or equal to 2%, greater than or equal to 3%, or greater than or equal to 5%. Films may be deposited on a flexible substrate (e.g., PET, a liquid crystalline polymer, and the like) comprising conductive traces. Then, a suitable property (e.g., dielectric breakdown voltage, dielectric constant, defect and/or pinhole concentration) may be assessed prior to elongation. The film may be elongated using an extensometer (e.g., an Instron 5900), and the suitable property may be measured again after elongation.

In accordance with certain embodiments, films synthesized by the methods described herein may comprise certain dielectric properties. Without wishing to be bound by theory, it is believed that the dielectric constant of a film may be influenced by the composition of the film. According to some embodiments, films comprising higher degrees of organic content may comprise lower dielectric constants. For example, in certain embodiments, films comprising more siloxane rings may comprise lower dielectric constants than films comprising fewer siloxane rings. In some embodiments, the films may comprise dielectric constants of greater than or equal to 2.6, greater than or equal to 2.65, greater than or equal to 2.7, greater than or equal to 2.75, greater than or equal greater than or equal to 2.8, greater than or equal to 2.85, greater than or equal to 2.9, greater than or equal to 2.95, greater than or equal to 3.0, greater than or equal to 3.05, greater than or equal to 3.1, or greater than or equal to 3.15. According to certain embodiments, the films may comprise dielectric constants of less than or equal to 3.2, less than or equal to 3.15, less than or equal to 3.1, less than or equal to 3.05, less than or equal to 3.0, less than or equal to 2.95, less than or equal to 2.9, less than or equal to 2.85, less than or equal to 2.8, less than or equal to 2.75, less than or equal to 2.7, or less than or equal to 2.65. Combinations of the above-referenced ranges are also possible (e.g., greater than or equal to 2.6 and less than or equal to 3.0, greater than or equal to 2.6 and less than or equal to 2.75, or greater than or equal to 2.6 and less than or equal to 2.7). Other ranges are also possible.

In certain embodiments, films may comprise dielectric constants that are unaffected or substantially unaffected by elongation. According to some embodiments, a dielectric constant variation may be defined as the absolute value of the difference between a dielectric constant of an elongated film and a dielectric constant of an initial film divided by the dielectric constant of the initial film. In accordance with certain embodiments, a film that has been elongated by 1%, or 2%, or 3%, or 5%, has a dielectric constant variation of greater than or equal to 0, greater than or equal to 0.025, greater than or equal to 0.05, greater than or equal to 0.075, greater than or equal to 0.1, greater than or equal to 0.15, greater than or equal to 0.2, greater than or equal to 0.25, or greater than or equal to 0.4. According to some embodiments, a film that has been elongated by 1% has a dielectric constant variation of less than or equal to 0.5, less than or equal to 0.4, less than or equal to 0.25, less than or equal to 0.2, less than or equal to 0.15, less than or equal to 0.1, less than or equal to 0.075, less than or equal to 0.05, or less than or equal to 0.025. Combinations of the above-referenced ranges are also possible (e.g., greater than or equal to 0 and less than or equal to 0.025, greater than or equal to 0 and less than or equal to 0.05, or greater than or equal to 0 and less than or equal to 1). Other ranges are also possible. One of ordinary skill in the art would be aware of methods for measuring the dielectric constant of a film. The dielectric constant of the films may be measured by using the procedure described in ASTM D150, which measures the AC loss and relative permittivity of the film as a function of frequency at 1 kHz and 1 MHz.

According to some embodiments, films may comprise a dielectric breakdown voltage. In certain embodiments, the films may comprise a dielectric breakdown voltage measured in the units of V/mil, where a mil is a unit of measurement equivalent to 0.001 inches. In some embodiments, the films may comprise a dielectric breakdown voltage of greater than or equal to 1000 V/mil, greater than or equal to 1500 V/mil, greater than or equal to 2000 V/mil, greater than or equal to 2500 V/mil, greater than or equal to 3000 V/mil, greater than or equal to 3500 V/mil, greater than or equal to 4000 V/mil, greater than or equal to 4500 V/mil, greater than or equal to 5000 V/mil, greater than or equal to 5500 V/mil, greater than or equal to 6000 V/mil, greater than or equal to 7500 V/mil, greater than or equal to 8000 V/mil, greater than or equal to 8500 V/mil, greater than or equal to 9000 V/mil, or greater than or equal to 9500 V/mil. According to certain embodiments, the films may comprise a dielectric breakdown voltage of less than or equal to 10000 V/mil, less than or equal to 9500 V/mil, less than or equal to 9000 V/mil, less than or equal to 8500 V/mil, less than or equal to 8000 V/mil, less than or equal to 7500 V/mil, less than or equal to 7000 V/mil, less than or equal to 6500 V/mil, less than or equal to 6000 V/mil, less than or equal to 5500 V/mil, less than or equal to 5000 V/mil, less than or equal to 4500 V/mil, less than or equal to 4000 V/mil, less than or equal to 3500 V/mil, less than or equal to 3000 V/mil, less than or equal to 2500 V/mil, less than or equal to 2000 V/mil, or less than or equal to 1500 V/mil. Combinations of the above-referenced ranges are also possible (e.g., greater than or equal to 2500 V/mil and less than or equal to 8500 V/mil, greater than or equal to 4000 V/mil and less than or equal to 7000 V/mil, or greater than or equal to 6000 V/mil and less than or equal to 10000 V/mil). Other ranges are also possible.

In certain embodiments, films may comprise dielectric breakdown voltages that are that are unaffected or substantially unaffected by elongation and/or flexing. According to some embodiments, a dielectric breakdown voltage variation may be defined as the absolute value of the difference between the dielectric breakdown voltage of an elongated film and a dielectric breakdown voltage of an initial film divided by the dielectric breakdown voltage constant of the initial film. In accordance with certain embodiments, a film that has been elongated by 1% or 2%, or 3%, or 5%, or which has undergone flexing, has a dielectric breakdown voltage variation of greater than or equal to 0, greater than or equal to 0.025, greater than or equal to 0.05, greater than or equal to 0.075, greater than or equal to 0.1, greater than or equal to 0.15, greater than or equal to 0.2, greater than or equal to 0.25, or greater than or equal to 0.4. According to some embodiments, a film that has been elongated by 1%, 2%, 3%, or 5%, or which has undergone flexing has a dielectric breakdown voltage variation of less than or equal to 0.5, less than or equal to 0.4, less than or equal to 0.25, less than or equal to 0.2, less than or equal to 0.15, less than or equal to 0.1, less than or equal to 0.075, less than or equal to 0.05, or less than or equal to 0.025. Combinations of the above-referenced ranges are also possible (e.g., greater than or equal to 0 and less than or equal to 0.025, greater than or equal to 0 and less than or equal to 0.05, or greater than or equal to 0 and less than or equal to 0.1). Other ranges are also possible.

The dielectric breakdown voltage of the films may be measured by ASTM D149 using the step by step method, which comprises exposing the film to a voltage that is raised uniformly from zero until the dielectric breakdown voltage is reached. Then, a fresh film is exposed to a voltage at 50% of the measured breakdown voltage and the voltage is increased in a stepwise manner until breakdown is reached. The dielectric breakdown voltage for the film is considered to be that measured using the stepwise test.

In some embodiments, films may retain a percentage of their initial adhesion strength after undergoing mechanical cycling. The percentage of initial adhesion strength retained may be defined as the adhesion strength of the film after undergoing flexing and/or elongation divided by the initial film adhesion strength. In accordance with certain embodiments, percentage of initial adhesion strength retained may be greater than or equal to 50%, greater than or equal to 75%, greater than or equal to 80%, greater than or equal to 85%, greater than or equal to 90%, greater than or equal to 95%, or greater than or equal to 99%. Other ranges are also possible. Flexing and elongating the films may comprise forming the films on a flexible substrate (e.g., LF20—please provide more details regarding this substrate) and then placing the flexible substrate over a hinge. The hinge then undergoes ten cycles, each of which comprise flexing the hinge to 130°, holding the hinge in this position for one second, returning the hinge to an unflexed position, and then holding the hinge in the unflexed position for one second. After this testing procedure, any suitable property of the films may be measured in a manner described herein.

The adhesion strength of a film may be determined by a method as described in ASTM D3359, which comprises making cuts in the film in a lattice pattern with eleven cuts in each direction, applying a pressure-sensitive tape over the cut, removing the pressure-sensitive tape, and assessing the adhesion by determining the extent of removal of the film. The percentage of adhesion strength retained after undergoing mechanical cycling is the ratio of the percent of the film within the lattice pattern that is retained by a film that has undergone mechanical cycling to the percent of the film within the lattice pattern that is retained by a film that has not undergone mechanical cycling.

In some embodiments, flexibility may be defined as the ability of a film to undergo mechanical cycling without forming more than a minimal number of cracks per millimeter along a bending direction as observed by optical microscopy. According to certain embodiments, the films may comprise a flexibility where the minimal number is zero. According to certain embodiments, mechanical cycling may comprise causing samples to undergo bending and unbending multiple times. For example, samples which comprise substrates and films deposited on the substrates may be fastened to a hinge and then the hinge may be flexed to an angle of approximately 130°. The hinge may remain flexed for approximately one second and then unflexed. The hinge may then remain unflexed for approximately one second. This cycle may be repeated for any number of times, such as ten times. Then, the samples may be removed from the hinge and examined using optical microscopy to determine crack formation.

According to certain embodiments, films comprising a high percentage of siloxane rings may be employed in one or more applications. In some embodiments, the films may be disposed upon and/or may be a component of a functional device. Non-limiting examples of functional devices include CMOS chips, RF devices, chips, and/or boards, transistors, ultra-high-speed mixed-signal circuits, power devices, switches, clock references, frequency selective filters, miniaturized arrays, digital to analog converters, analog to digital converters, low noise amplifiers, and/or MEMS devices. In some embodiments, a film comprising a high percentage of siloxane rings may be disposed on the surface of an electronic circuit to reduce or prevent moisture and/or mechanical damage. For example, In one exemplary embodiment, a polymeric thin film may be formed via reaction of at least one monomer comprising a cyclic siloxane monomer and at least one vinyl group, wherein substantially all of the cyclic siloxane groups are retained in the polymer and the polymer coats at least a portion of or substantially coats the functional device.

In some embodiments, the functional device is an RF device. As will be known to those of ordinary skill in the art, an RF device is an electronic device that involves radio frequency electronics. In some embodiments, the RF device is used to transmit and/or receive radio signals. Non-limiting examples of RF devices include RF integrated circuits, RFID integrated circuits, RFID tags, and other RF transceivers and transponders. The RF device may or may not include an internal antenna element. In some embodiments, the RF device is a high frequency RF device. Other RF devices include, but are not limited to, MIMCs, transmission lines, filters, oscillators. In some embodiments, the RF device is a high frequency RF device, wherein the high frequency RF device operates at a frequency greater than about 100 MHz, greater than about 250 MHz, greater than about 500 MHz, greater than about 1 GHz, greater than about 2.5 GHz, greater than about 5 GHz, greater than about 10 GHz, greater than about 25 GHz, greater than about 50 GHz, or greater than about 100 GHz. The high frequency RF device may operate at a frequency of less than about 250 GHz, less than about 100 GHz, less than about 50 GHz, less than about 25 GHz, less than about 10 GHz, less than about 5 GHz, less than about 2.5 GHz, less than about 1 GHz, less than about 500 MHz, or less than about 250 MHz. Combinations of the above-referenced ranges are also possible (e.g., greater than about 100 MHz and less than about 250 GHz). Other ranges are also possible.

In one specific non-limiting embodiment, a polymer described herein is deposited directly upon an RF device (or another functional device). In some embodiments, the deposition of the polymer film as described herein on the RF has a minimal impact on device performance. For example, in some embodiments, a device comprising a polymer described herein or formed by the methods described herein may change the output (e.g., RF response signal) from the device by less than about 25%, or about 20% or about 15%, or about 10%, or about 5%, or about 2%, or about 1% for a given input as compared to a substantially similar device but not comprising a polymer described herein or formed by the methods described herein. In some embodiments, a device comprising a polymer described herein or formed by the methods described herein may change the output (e.g., RF response signal) from the device by less than about 10 dB, less than about 5 dB, less than about 2.5 dB, less than about 1 dB, or less than about 0.5 dB. In some embodiments, the variation may occur at a frequency in the range of about 0.1 GHz to about 10 GHz, about 10 GHz to 100 GHz, or about 10 GHz to about 250 GHz.

In another embodiment, a change in RF response signal from a coated device may be observed subsequent to device coating when the device is activated in the frequency range 0.1-100 GHz, but the change in the RF response signal will be that arising from a well-behaved dielectric. As used herein, a well-behaved dielectric is a material that has an unvarying effect on response signal across the relevant range of frequencies (i.e., the frequencies over which it is a well-behaved dielectric; such as between 0.1 GHz and 100 GHz) that does not decrease the signal to noise ratio of the response signal. As is known to those of ordinary skill in the art, the effect of well-behaved dielectric materials can be understood and accounted for by those designing RF devices without requiring substantial experimentation. Some well-behaved dielectric materials may be accurately modeled, obviating the need for any experiments to be performed to determine their effect on device performance.

In some embodiments, the films described herein (e.g., films disposed on RF devices as described herein, films disposed on biological devices as described herein) may be capable of maintaining one or more of their properties (e.g., siloxane ring content, vinyl group content, water vapor permeability, freedom from defects, dielectric constant, dielectric breakdown voltage, adhesion strength, and the like) for a significant period of time. For instance, the films may maintain one or more of these properties for a time period of at least one day, at least one week, at least one month, at least one year, at least 10 years, at least 25 years, or at least 100 years. In some embodiments, the films may exhibit a change in the dielectric breakdown voltage and/or dielectric constant of less than 25%, less than 10%, less than 5%, less than 2%, or less than 1% over the course of at least one day, at least one week, at least one month, at least one year, at least 10 years, at least 25 years, or at least 100 years.

As described herein, in certain embodiments, films may be disposed on functional devices which comprise one or more semiconductors. Non-limiting examples of semiconductor materials are described herein. Such semiconductors may be desirable for use in a functional device as they may be capable of forming features of high complexity and integration while also providing high levels of yield and manufacturability. In certain embodiments, the semiconductor(s) may have certain beneficial properties, such as a high carrier velocity, a high peak velocity, a high voltage swing, a high charge density, a high thermal conductivity, and/or a high breakdown voltage. In some embodiments, the semiconductor(s) may comprise or form complex circuitry.

According to some embodiments, the functional device may comprise structures which comprise one or more semiconductor materials, for example, heterojunction bipolar transistors, high-electron mobility transistors, amplifiers, and/or amplifier chains. In some embodiments, the functional device may comprise indium phosphide heterojunction bipolar transistors, amplifiers, and/or amplifier chains. In certain embodiments, the functional device may comprise gallium nitride high-electron mobility transistors, amplifiers, and/or amplifier chains.

In some embodiments, the functional device may comprise both silicon and one or more other semiconductor materials. For example, in some certain embodiments, the functional device may comprise indium phosphide and silicon, such as in an indium phosphide bipolar CMOS integrated circuit. The indium phosphide bipolar CMOS circuit may comprise both indium phosphide heterojunction bipolar transistors and silicon CMOS. According to some embodiments, the functional device may comprise gallium nitride and silicon. For instance, the functional device may comprise gallium nitride high-electron-mobility transistors and silicon CMOS. In some embodiments, the functional device may comprise indium phosphide, gallium nitride, and silicon. In certain embodiments, the device may comprise indium phosphide heterojunction bipolar transistors, gallium nitride high-electron-mobility transistors, and silicon CMOS. Other combinations of semiconductors and compound semiconductors are also possible.

In embodiments, for devices which comprise silicon and one or more other semiconductor materials, the silicon and other semiconductor(s) may be integrated together (e.g., by heterogeneous integration, or integration of two different materials within one functional device). Integration may comprise package and/or IC stacking with wire bond and/or flip-chip interconnects, in accordance with some embodiments. In certain embodiments, the integration may comprise chip to wafer integration, such as in devices which comprise a passive silicon interposer with thru silicon vias and interconnects. In some embodiments, the integration may comprise wafer level integration, such as in devices that comprise through silicon vias through active stacked devices. According to certain embodiments, wafer level integration may take the form of face to face wafer bonding of active devices.

According to certain embodiments, films having a high percentage of siloxane rings may be deposited on medical devices. In some embodiments, films having a high percentage of siloxane rings may be deposited on medical devices designed to be implanted in the body or disposed on the body. The devices may be electronic medical devices, or medical devices that comprise digital electronics. The devices may be have any suitable function and may be used at any suitable location within or on the body, some of which are described below. In some embodiments, the film may be one layer of several on the device. The film may be an interstitial layer (e.g., a layer between two other layers), it may be the outermost layer, or it may be the innermost layer. In some embodiments, it may be preferred for the film to be an interstitial layer positioned between two low permeability layers.

In embodiments in which the film is deposited on a medical device, the medical device may be any suitable medical device, non-limiting examples of which are described below. For instance, the films may be deposited on medical devices suitable for being implanted into the eye (e.g., retinal implants, retinal prostheses, and smart contact lenses); suitable for stimulating nerves (e.g., phrenic nerve stimulators, breathing pacemaker systems, and diaphragm pacing systems); suitable for use as sensors (e.g., implantable glucose sensors); suitable for being implanted in or used on the ear (e.g., cochlear implants); suitable for use with the heart (e.g., pacemakers and defibrillators); suitable for use with the bladder (e.g., sacral anterior root stimulators); suitable for pain management (e.g., occipital nerve stimulators and spinal cord stimulators); suitable for use in the treatment of Parkinson's disease and/or Dystonia (e.g., deep brain stimulators); suitable for use in the treatment of epilepsy (e.g., neurostimulators and vagus nerve stimulators); suitable for stimulating peripheral nerves (e.g., drop foot stimulators and handgrip stimulators); suitable for stimulating the lower esophagus; suitable for use in vagal blocking therapy; suitable for use as a component of an implantable drug delivery system (e.g., implantable pumps, electromagnetic micropumps, osmotic micropumps, electroosmotic micropumps, electrolysis micropumps, constant flow infusion pumps, ophthalmic micropumps, and wireless microchip drug delivery systems); suitable for use as a wireless endoscopy capsule; and/or suitable for use in the central nervous system (e.g., capable of reading activation potentials in single cells and/or nerve bundles). The films may also be deposited on medical devices not listed herein.

In some embodiments, a film deposited on a medical device may be capable of protecting the device from a biological environment to which the device is exposed. The presence of the film on the device may eliminate or reduce the tendency of the device to undergo shorting, corrosion, and/or increased signal to noise over its lifetime in comparison to an otherwise equivalent device that does not comprise the film. In some embodiments, the device comprising the film may have any one of the properties described herein after being exposed to a biological environment or biological fluid for a time period of at least one day, at least one week, at least one month, at least one year, at least 10 years, at least 25 years, or at least 100 years.

Those of ordinary skill in the art will be aware of methods and systems for exposing a device to a biological environment or biological fluid. The term "biological environment" is given its ordinary meaning in the art and generally refers to the body of a subject (e.g., a mammalian patient such as a human patient). However, the term "biological environment" can also include an in vitro environment that models a desired in vivo environment (e.g., a temperature of about 37° C. and saline or Ringer's solution). In some embodiments, the device may be exposed to a biological environment or a biological fluid via implantation within or on a subject (e.g., a human) For example, the device may be implanted in the ear, eye, heart, liver, kidney, stomach, skin, nervous system, spinal cord, brain, bladder, esophagus, etc., of a subject. Non-limiting examples of biological fluids include saliva, whole blood, plasma, serum, lymph, synovial fluid, peritoneal fluid, pleural fluid, urine, sputum, semen, vaginal lavage, bone marrow, cerebrospinal cord fluid, and tears. In some embodiments, the testing may be carried out using a biological fluid substitute (e.g., saline).

In some embodiments, the film may exhibit a leakage current of less than or equal to $10^{-15}$ A, less than or equal to $10^{-14}$ A, less than or equal to $10^{-13}$ A, less than or equal to $10^{-12}$ A, less than or equal to $10^{-10}$ A, or less than or equal to $10^{-8}$ A after being exposed to a biological environment or biological fluid for a time period of at least one day, at least one week, at least one month, at least 1 year, at least 2 years, at least 3 years, at least 4 years, at least 5 years, at least 10 years, at least 20 years, at least 25 years, or at least 100 years. Leakage current may be determined by placing the device in salt water and measuring the current flow through the coating.

In some embodiments, the film may exhibit a dielectric breakdown voltage of greater than or equal to 5000 V/mil after being exposed to a biological environment or biological fluid for a time period of at least one day, at least one week, at least one month, at least 1 year, at least 2 years, at least 3 years, at least 4 years, at least 5 years, at least 10 years, at least 20 years, at least 25 years, or at least 100 years. In some embodiments, the films may exhibit a dielectric breakdown voltage that is within 25%, within 10%, within 5%, within 2%, or within 1% of an otherwise identical film that has not been exposed to a biological environment or biological fluid after being exposed to a biological environment or biological fluid for a time period of at least one day, at least one week, at least one month, at least 1 year, at least 2 years, at least 3 years, at least 4 years, at least 5 years, at least 10 years, at least 20 years, at least 25 years, or at least 100 years. The dielectric breakdown voltage of the film may be measured by ASTM D149 as described above.

In some embodiments, the device comprising the film may be free from short circuits after being exposed to a biological environment or fluid and being subject to a dc bias voltage of at least 1 V, at least 5 V, at least 20 V, at least 100 V, or at least 500 V for a time period of at least one day, at least one week, at least one month, at least 1 year, at least 2 years, at least 3 years, at least 4 years, at least 5 years, at least 10 years, at least 20 years, at least 25 years, or at least 100 years. In some embodiments, the device comprising the film may be free from short circuits after being exposed to a biological environment or fluid and being subject to a ac bias voltage of at least 1 V, at least 5 V, at least 20 V, at least 100 V, or at least 500 V for a time period of at least one day, at least one week, at least one month, at least 1 year, at least 2 years, at least 3 years, at least 4 years, at least 5 years, at least 10 years, at least 20 years, at least 25 years, or at least 100 years. In some embodiments, the device comprising the film may have substantially fewer short circuits (e.g., 10% fewer, 25% fewer, 50% fewer) short circuits than an otherwise equivalent device not comprising the film after being exposed to a biological environment or fluid and being subject to a dc bias voltage of at least 1 V, at least 5 V, at least 20 V, at least 100 V, or at least 500 V for a time period of at least one day, at least one week, at least one month, 1 year, at least 2 years, at least 3 years, at least 4 years, at least 5 years, at least 10 years, at least 20 years, at least 25 years, or at least 100 years. In some embodiments, the device comprising the film may have substantially fewer short circuits (e.g., 10% fewer, 25% fewer, 50% fewer) short circuits than an otherwise equivalent device not comprising the film after being exposed to a biological environment or fluid and being subject to a ac bias voltage of at least 1 V, at least 5 V, at least 20 V, at least 100 V, or at least 500 V for a time period of at least one day, at least one week, at least one month, at least 1 year, at least 2 years, at least 3 years, at least 4 years, at least 5 years, at least 10 years, at least 20 years, at least 25 years, or at least 100 years. As used herein, short circuits are electrical connections between device components that occur during device operation and allow a current to flow along a lower resistance pathway than the pathway that results in device operation. Short circuits can be detected by monitoring device performance; a sharp drop in device performance indicates the formation of a short circuit.

In some embodiments, the device comprising the film may be free from corrosion after being exposed to a biological environment or fluid for a time period of at least one day, at least one week, at least one month, at least 1 year, at least 2 years, at least 3 years, at least 4 years, at least 5 years, at least 10 years, at least 20 years, at least 25 years, or at least 100 years. In some embodiments, the device comprising the film may have less corrosion (e.g., 10% less, 25% less, 50% less) corrosion than an otherwise equivalent device not comprising the film after being exposed to a biological environment or fluid and being subject to a dc bias voltage of at least 1 V, at least 5 V, at least 20 V, or at least 100 V for a time period of at least one day, at least one week, at least one month, 1 year, at least 2 years, at least 3 years, at least 4 years, at least 5 years, at least 10 years, at least 20 years, at least 25 years, or at least 100 years. As used herein, corrosion refers to the reaction of a metal (e.g., with water, with oxygen) such that the metal reacts to form a compound which is present at least the surface of the metal. Corrosion may be detected by a decrease in the functionality of the device as electrical resistance increases across the corroded part. Devices that are substantially free from corrosion have substantially no decrease in functionality; devices which have some corrosion may provide an output signal that is partially reduced (e.g., a film that is 10% corroded may have an output signal that is 10% less than an otherwise equivalent device that is uncorroded).

In some embodiments, the percent change in the signal to noise ratio of the device comprising the film after being exposed to a biological environment or biological fluid for a time period of at least one day, at least one week, at least one month, at least 1 year, at least 2 years, at least 3 years, at least 4 years, at least 5 years, at least 10 years, at least 20 years, at least 25 years, or at least 100 years may be less than or equal to 25%, less than or equal to 10%, less than or equal to 5%, less than or equal to 2%, or less than or equal to 1%. In some embodiments, the percent change in the signal to noise ratio of the device comprising the film after being exposed to a biological environment or biological fluid for a time period of at least one day, at least one week, at least one month, at least 1 year, at least 2 years, at least 3 years, at least 4 years, at least 5 years, at least 10 years, at least 20 years, at least 25 years, or at least 100 years may be substantially less than an otherwise equivalent device not comprising the film (e.g., 10% less, 25% less, 50% less).

In some embodiments, the film may be flexible as described herein after being exposed to a biological environment or biological fluid for a time period of at least one day, at least one week, at least one month, at least 1 year, at least 2 years, at least 3 years, at least 4 years, at least 5 years, at least 10 years, at least 20 years, at least 25 years, or at least 100 years. In some embodiments, a device comprising the film may be substantially more flexible (e.g., 10% more, 25% more, 50% more) than an otherwise equivalent device not comprising the film after being exposed to a biological environment or biological fluid for a time period of at least one day, at least one week, at least one month, at least 1 year, at least 2 years, at least 3 years, at least 4 years, at least 5 years, at least 10 years, at least 20 years, at least 25 years, or at least 100 years.

In some embodiments, the film may retain at least 50%, at least 75%, at least 80%, at least 85%, at least 90%, at least 95%, or at least 99% of their initial adhesion after being exposed to a biological environment or biological fluid for a time period of at least one day, at least one week, at least one month, at least 1 year, at least 2 years, at least 3 years, at least 4 years, at least 5 years, at least 10 years, at least 20 years, at least 25 years, or at least 100 years. In some embodiments, the film may be a biocompatible material, such as a USP Class VI material.

Definitions

For convenience, certain terms employed in the specification, examples, and appended claims are listed here.

As used herein, the term "reacting" refers to the forming of a bond between two or more components to produce a stable, isolable compound. For example, a first component and a second component may react to form one reaction product comprising the first component and the second component joined by a covalent bond. That is, the term "reacting" does not refer to the interaction of solvents, catalysts, bases, ligands, or other materials which may serve to promote the occurrence of the reaction with the component(s).

Definitions of specific functional groups and chemical terms are described in more detail below. For purposes of this invention, the chemical elements are identified in accordance with the Periodic Table of the Elements, CAS version, *Handbook of Chemistry and Physics*, 75$^{th}$ Ed., inside cover, and specific functional groups are generally defined as described therein. Additionally, general principles of organic chemistry, as well as specific functional moieties and reactivity, are described in *Organic Chemistry*, Thomas Sorrell, University Science Books, Sausalito: 1999, the entire contents of which are incorporated herein by reference.

The term "aliphatic," as used herein, includes both saturated and unsaturated, nonaromatic, straight chain (i.e., unbranched), branched, acyclic, and cyclic (i.e., carbocyclic) hydrocarbons, which are optionally substituted with one or more functional groups. As will be appreciated by one of ordinary skill in the art, "aliphatic" is intended herein to include, but is not limited to, alkyl, alkenyl, alkynyl, cycloalkyl, cycloalkenyl, and cycloalkynyl moieties. Thus, as used herein, the term "alkyl" includes straight, branched and cyclic alkyl groups. An analogous convention applies to other generic terms such as "alkenyl", "alkynyl", and the like. Furthermore, as used herein, the terms "alkyl", "alkenyl", "alkynyl", and the like encompass both substituted and unsubstituted groups. In certain embodiments, as used herein, "aliphatic" is used to indicate those aliphatic groups (cyclic, acyclic, substituted, unsubstituted, branched or unbranched) having 1-20 carbon atoms. Aliphatic group substituents include, but are not limited to, any of the substituents described herein, that result in the formation of a stable moiety (e.g., aliphatic, alkyl, alkenyl, alkynyl, heteroaliphatic, heterocyclic, aryl, heteroaryl, acyl, oxo, imino, thiooxo, cyano, isocyano, amino, azido, nitro, hydroxyl, thiol, halo, aliphaticamino, heteroaliphaticamino, alkylamino, heteroalkylamino, arylamino, heteroarylamino, alkylaryl, arylalkyl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, acyloxy, and the like, each of which may or may not be further substituted).

As used herein, the term "alkyl" is given its ordinary meaning in the art and refers to the radical of saturated aliphatic groups, including straight-chain alkyl groups, branched-chain alkyl groups, cycloalkyl (alicyclic) groups, alkyl substituted cycloalkyl groups, and cycloalkyl substituted alkyl groups. In some cases, the alkyl group may be a lower alkyl group, i.e., an alkyl group having 1 to 10 carbon atoms (e.g., methyl, ethyl, propyl, butyl, pentyl, hexyl, heptyl, octyl, nonyl, or decyl). In some embodiments, a straight chain or branched chain alkyl may have 30 or fewer carbon atoms in its backbone, and, in some cases, 20 or fewer. In some embodiments, a straight chain or branched chain alkyl may have 12 or fewer carbon atoms in its backbone (e.g., $C_1$-$C_{12}$ for straight chain, $C_3$-$C_{12}$ for branched chain), 6 or fewer, or 4 or fewer. Likewise, cycloalkyls may have from 3-10 carbon atoms in their ring structure, or 5, 6 or 7 carbons in the ring structure. Examples of alkyl groups include, but are not limited to, methyl, ethyl, propyl, isopropyl, cyclopropyl, butyl, isobutyl, t-butyl, cyclobutyl, hexyl, and cyclochexyl.

The term "alkylene" as used herein refers to a bivalent alkyl group. An "alkylene" group is a polymethylene group, i.e., $-(CH_2)_z-$, wherein z is a positive integer, e.g., from 1 to 20, from 1 to 10, from 1 to 6, from 1 to 4, from 1 to 3, from 1 to 2, or from 2 to 3. A substituted alkylene chain is a polymethylene group in which one or more methylene hydrogen atoms are replaced with a substituent. Suitable substituents include those described herein for a substituted aliphatic group.

Generally, the suffix "-ene" is used to describe a bivalent group. Thus, any of the terms defined herein can be modified with the suffix "-ene" to describe a bivalent version of that moiety. For example, a bivalent carbocycle is "carbocyclylene", a bivalent aryl ring is "arylene", a bivalent benzene ring is "phenylene", a bivalent heterocycle is "heterocyclylene", a bivalent heteroaryl ring is "heteroarylene", a bivalent alkyl chain is "alkylene", a bivalent alkenyl chain is "alkenylene", a bivalent alkynyl chain is "alkynylene", a bivalent heteroalkyl chain is "heteroalkylene", a bivalent heteroalkenyl chain is "heteroalkenylene", a bivalent heteroalkynyl chain is "heteroalkynylene", and so forth.

The terms "alkenyl" and "alkynyl" are given their ordinary meaning in the art and refer to unsaturated aliphatic groups analogous in length and possible substitution to the alkyls described above, but that contain at least one double or triple bond respectively.

In certain embodiments, the alkyl, alkenyl and alkynyl groups employed in the invention contain 1-20 aliphatic carbon atoms. In certain other embodiments, the alkyl, alkenyl, and alkynyl groups employed in the invention contain 1-10 aliphatic carbon atoms. In yet other embodiments, the alkyl, alkenyl, and alkynyl groups employed in the invention contain 1-8 aliphatic carbon atoms. In still other embodiments, the alkyl, alkenyl, and alkynyl groups employed in the invention contain 1-6 aliphatic carbon atoms. In yet other embodiments, the alkyl, alkenyl, and alkynyl groups employed in the invention contain 1-4 carbon atoms. Illustrative aliphatic groups thus include, but are not limited to, for example, methyl, ethyl, n-propyl, isopropyl, allyl, n-butyl, sec-butyl, isobutyl, t-butyl, n-pentyl, sec-pentyl, isopentyl, t-pentyl, n-hexyl, sec-hexyl, moieties and the like, which again, may bear one or more substituents. Alkenyl groups include, but are not limited to, for example, ethenyl, propenyl, butenyl, 1-methyl-2-buten-1-yl, and the like. Representative alkynyl groups include, but are not limited to, ethynyl, 2-propynyl (propargyl), 1-propynyl and the like.

The term "cycloalkyl," as used herein, refers specifically to groups having three to ten, preferably three to seven carbon atoms. Suitable cycloalkys include, but are not limited to cyclopropyl, cyclobutyl, cyclopentyl, cyclohexyl, cycloheptyl and the like, which, as in the case of other aliphatic, heteroaliphatic, or hetercyclic moieties, may optionally be substituted with substituents including, but not limited to aliphatic; heteroaliphatic; aryl; heteroaryl; arylalkyl; heteroarylalkyl; alkoxy; aryloxy; heteroalkoxy; heteroaryloxy; alkylthio; arylthio; heteroalkylthio; heteroarylthio; $-F$; $-Cl$; $-Br$; $-I$; $-OH$; $-NO_2$; $-CN$; $-CF_3$; $-CH_2CF_3$; $-CHCl_2$; $-CH_2OH$; $-CH_2CH_2OH$; $-CH_2NH_2$; $-CH_2SO_2CH_3$; $-C(O)R_x$; $-CO_2(R_x)$; $-CON(R_x)_2$; $-OC(O)R_x$; $-OCO_2R_x$; $-OCON(R_x)_2$; $-N(R_c)_2$; $-S(O)_2R_x$; $-NR_x(CO)R_x$, wherein each occurrence of $R_x$ independently includes, but is not limited to, aliphatic, heteroaliphatic, aryl, heteroaryl, arylalkyl, or heteroarylkyl, wherein any of the aliphatic, heteroaliphatic, arylalkyl, or heteroarylalkyl substituents described above and herein may be substituted or unsubstituted, branched or unbranched, cyclic or acyclic, and wherein any of the aryl or heteroaryl substituents described above and herein may be substituted or unsubstituted. Additional examples of generally applicable substituents are illustrated by the specific embodiments shown in the Examples that are described herein.

The term "heteroaliphatic," as used herein, refers to an aliphatic moiety, as defined herein, which includes both saturated and unsaturated, nonaromatic, straight chain (i.e., unbranched), branched, acyclic, cyclic (i.e., heterocyclic), or polycyclic hydrocarbons, which are optionally substituted with one or more functional groups, and that contain one or more oxygen, sulfur, nitrogen, phosphorus, or silicon atoms, e.g., in place of carbon atoms. In certain embodiments, heteroaliphatic moieties are substituted by independent replacement of one or more of the hydrogen atoms thereon with one or more substituents. As will be appreciated by one of ordinary skill in the art, "heteroaliphatic" is intended herein to include, but is not limited to, heteroalkyl, heteroalkenyl, heteroalkynyl, heterocycloalkyl, heterocycloalkenyl, and heterocycloalkynyl moieties. Thus, the term "heteroaliphatic" includes the terms "heteroalkyl," "heteroalkenyl", "heteroalkynyl", and the like. Furthermore, as used herein, the terms "heteroalkyl", "heteroalkenyl", "heteroalkynyl", and the like encompass both substituted and unsubstituted groups. In certain embodiments, as used herein, "heteroaliphatic" is used to indicate those heteroaliphatic groups (cyclic, acyclic, substituted, unsubstituted, branched or unbranched) having 1-20 carbon atoms. Heteroaliphatic group substituents include, but are not limited to, any of the substituents described herein, that result in the formation of a stable moiety (e.g., aliphatic, alkyl, alkenyl, alkynyl, heteroaliphatic, heterocyclic, aryl, heteroaryl, acyl, sulfinyl, sulfonyl, oxo, imino, thiooxo, cyano, isocyano, amino, azido, nitro, hydroxyl, thiol, halo, aliphaticamino, heteroaliphaticamino, alkylamino, heteroalkylamino, arylamino, heteroarylamino, alkylaryl, arylalkyl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, acyloxy, and the like, each of which may or may not be further substituted).

The term "heteroalkyl" is given its ordinary meaning in the art and refers to an alkyl group as described herein in which one or more carbon atoms is replaced by a heteroatom. Suitable heteroatoms include oxygen, sulfur, nitrogen, phosphorus, and the like. Examples of heteroalkyl groups include, but are not limited to, alkoxy, alkoxyalkyl, amino, thioester, poly(ethylene glycol), and alkyl-substituted amino.

The terms "heteroalkenyl" and "heteroalkynyl" are given their ordinary meaning in the art and refer to unsaturated aliphatic groups analogous in length and possible substitution to the heteroalkyls described above, but that contain at least one double or triple bond respectively.

Some examples of substituents of the above-described aliphatic (and other) moieties of compounds of the invention include, but are not limited to aliphatic; heteroaliphatic; aryl; heteroaryl; alkylaryl; alkylheteroaryl; alkoxy; aryloxy; heteroalkoxy; heteroaryloxy; alkylthio; arylthio; heteroalkylthio; heteroarylthio; F; Cl; Br; I; $-OH$; $-NO_2$; $-CN$; $-CF_3$; $-CHF_2$; $-CH_2F$; $-CH_2CF_3$; $-CHCl_2$; $-CH_2OH$; $-CH_2CH_2OH$; $-CH_2NH_2$; $-CH_2SO_2CH_3$; $-C(O)R_x$; $-CO_2(R_x)$; $-CON(R_x)_2$; $-OC(O)R_x$;

—OCO$_2$R$_x$; —OCON(R$_x$)$_2$; —N(R$_x$)$_2$; —S(O)$_2$R$_x$; —NR$_x$(CO)R$_x$ wherein each occurrence of R$_x$ independently includes, but is not limited to, aliphatic, alycyclic, heteroaliphatic, heterocyclic, aryl, heteroaryl, alkylaryl, or alkylheteroaryl, wherein any of the aliphatic, heteroaliphatic, alkylaryl, or alkylheteroaryl substituents described above and herein may be substituted or unsubstituted, branched or unbranched, cyclic or acyclic, and wherein any of the aryl or heteroaryl substituents described above and herein may be substituted or unsubstituted. Additional examples of generally applicable substituents are illustrated by the specific embodiments shown in the Examples that are described herein.

The term "aryl" is given its ordinary meaning in the art and refers to aromatic carbocyclic groups, optionally substituted, having a single ring (e.g., phenyl), multiple rings (e.g., biphenyl), or multiple fused rings in which at least one is aromatic (e.g., 1,2,3,4-tetrahydronaphthyl, naphthyl, anthryl, or phenanthryl). That is, at least one ring may have a conjugated pi electron system, while other, adjoining rings can be cycloalkyls, cycloalkenyls, cycloalkynyls, aryls and/or heterocyclyls. The aryl group may be optionally substituted, as described herein. Substituents include, but are not limited to, any of the previously mentioned substituents, i.e., the substituents recited for aliphatic moieties, or for other moieties as disclosed herein, resulting in the formation of a stable compound. In some cases, an aryl group is a stable mono- or polycyclic unsaturated moiety having preferably 3-14 carbon atoms, each of which may be substituted or unsubstituted. "Carbocyclic aryl groups" refer to aryl groups wherein the ring atoms on the aromatic ring are carbon atoms. Carbocyclic aryl groups include monocyclic carbocyclic aryl groups and polycyclic or fused compounds (e.g., two or more adjacent ring atoms are common to two adjoining rings) such as naphthyl groups.

The terms "heteroaryl" is given its ordinary meaning in the art and refers to aryl groups comprising at least one heteroatom as a ring atom. A "heteroaryl" is a stable heterocyclic or polyheterocyclic unsaturated moiety having preferably 3-14 carbon atoms, each of which may be substituted or unsubstituted. Substituents include, but are not limited to, any of the previously mentioned substituents, i.e., the substitutes recited for aliphatic moieties, or for other moieties as disclosed herein, resulting in the formation of a stable compound. In some cases, a heteroaryl is a cyclic aromatic radical having from five to ten ring atoms of which one ring atom is selected from S, O, and N; zero, one, or two ring atoms are additional heteroatoms independently selected from S, O, and N; and the remaining ring atoms are carbon, the radical being joined to the rest of the molecule via any of the ring atoms, such as, for example, pyridyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, furanyl, quinolinyl, isoquinolinyl, and the like.

It will also be appreciated that aryl and heteroaryl moieties, as defined herein may be attached via an alkyl or heteroalkyl moiety and thus also include -(alkyl)aryl, -(heteroalkyl)aryl, -(heteroalkyl)heteroaryl, and -(heteroalkyl)heteroaryl moieties. Thus, as used herein, the phrases "aryl or heteroaryl moieties" and "aryl, heteroaryl, -(alkyl)aryl, -(heteroalkyl)aryl, -(heteroalkyl)heteroaryl, and -(heteroalkyl)heteroaryl" are interchangeable. Substituents include, but are not limited to, any of the previously mentioned substituents, i.e., the substituents recited for aliphatic moieties, or for other moieties as disclosed herein, resulting in the formation of a stable compound.

It will be appreciated that aryl and heteroaryl groups (including bicyclic aryl groups) can be unsubstituted or substituted, wherein substitution includes replacement of one or more of the hydrogen atoms thereon independently with any one or more of the following moieties including, but not limited to: aliphatic; alicyclic; heteroaliphatic; heterocyclic; aromatic; heteroaromatic; aryl; heteroaryl; alkylaryl; heteroalkylaryl; alkylheteroaryl; heteroalkylheteroaryl; alkoxy; aryloxy; heteroalkoxy; heteroaryloxy; alkylthio; arylthio; heteroalkylthio; heteroarylthio; F; Cl; Br; I; —OH; —NO$_2$; —CN; —CF$_3$; —CH$_2$F; —CHF$_2$; —CH$_2$CF$_3$; —CHCl$_2$; —CH$_2$OH; —CH$_2$CH$_2$OH; —CH$_2$NH$_2$; —CH$_2$SO$_2$CH$_3$; —C(O)R$_x$; —CO$_2$(R$_x$); —CON(R$_x$)$_2$; —OC(O)R$_x$; —OCO$_2$R$_x$; —OCON(R$_x$)$_2$; —N(R$_x$)$_2$; —S(O)R$_x$; —S(O)$_2$R$_x$; —NR$_x$(CO)R$_x$ wherein each occurrence of R$_x$ independently includes, but is not limited to, aliphatic, alicyclic, heteroaliphatic, heterocyclic, aromatic, heteroaromatic, aryl, heteroaryl, alkylaryl, alkylheteroaryl, heteroalkylaryl or heteroalkylheteroaryl, wherein any of the aliphatic, alicyclic, heteroaliphatic, heterocyclic, alkylaryl, or alkylheteroaryl substituents described above and herein may be substituted or unsubstituted, branched or unbranched, saturated or unsaturated, and wherein any of the aromatic, heteroaromatic, aryl, heteroaryl, -(alkyl)aryl or -(alkyl)heteroaryl substituents described above and herein may be substituted or unsubstituted. Additionally, it will be appreciated, that any two adjacent groups taken together may represent a 4, 5, 6, or 7-membered substituted or unsubstituted alicyclic or heterocyclic moiety. Additional examples of generally applicable substituents are illustrated by the specific embodiments described herein.

The terms "halo" and "halogen" as used herein refer to an atom selected from the group consisting of fluorine, chlorine, bromine, and iodine.

It will be appreciated that the above groups and/or compounds, as described herein, may be optionally substituted with any number of substituents or functional moieties. That is, any of the above groups may be optionally substituted. As used herein, the term "substituted" is contemplated to include all permissible substituents of organic compounds, "permissible" being in the context of the chemical rules of valence known to those of ordinary skill in the art. In general, the term "substituted" whether preceded by the term "optionally" or not, and substituents contained in formulas of this invention, refer to the replacement of hydrogen radicals in a given structure with the radical of a specified substituent. When more than one position in any given structure may be substituted with more than one substituent selected from a specified group, the substituent may be either the same or different at every position. It will be understood that "substituted" also includes that the substitution results in a stable compound, e.g., which does not spontaneously undergo transformation such as by rearrangement, cyclization, elimination, etc. In some cases, "substituted" may generally refer to replacement of a hydrogen with a substituent as described herein. However, "substituted," as used herein, does not encompass replacement and/or alteration of a key functional group by which a molecule is identified, e.g., such that the "substituted" functional group becomes, through substitution, a different functional group. For example, a "substituted phenyl group" must still comprise the phenyl moiety and cannot be modified by substitution, in this definition, to become, e.g., a pyridine ring. In a broad aspect, the permissible substituents include acyclic and cyclic, branched and unbranched, carbocyclic and heterocyclic, aromatic and nonaromatic substituents of organic compounds. Illustrative substituents include, for example, those described herein. The permissible substituents can be one or more and the same or different for appropriate organic compounds. For purposes of this invention, the heteroatoms such as nitrogen may have hydrogen substituents and/or any permissible substituents of organic compounds described herein which satisfy the valencies of the heteroatoms. Furthermore, this invention is not intended to be limited in any manner by the permissible substituents of organic compounds. The term "stable," as used herein, preferably refers to compounds which possess stability sufficient to allow manufacture and which maintain the integrity of the compound for a sufficient period of time to be detected and preferably for a sufficient period of time to be useful for the purposes detailed herein.

Examples of substituents include, but are not limited to, halogen, azide, alkyl, aralkyl, alkenyl, alkynyl, cycloalkyl, hydroxyl, alkoxyl, amino, nitro, sulfhydryl, imino, amido, phosphonate, phosphinate, carbonyl, carboxyl, silyl, ether, alkylthio, sulfonyl, sulfonamido, ketone, aldehyde, ester, heterocyclyl, aromatic or heteroaromatic moieties, —$CF_3$, —CN, aryl, aryloxy, perhaloalkoxy, aralkoxy, heteroaryl, heteroaryloxy, heteroarylalkyl, heteroaralkoxy, azido, amino, halide, alkylthio, oxo, acylalkyl, carboxy esters, -carboxamido, acyloxy, aminoalkyl, alkylaminoaryl, alkylaryl, alkylaminoalkyl, alkoxyaryl, arylamino, aralkylamino, alkylsulfonyl, -carboxamidoalkylaryl, -carboxamidoaryl, hydroxyalkyl, haloalkyl, alkylaminoalkylcarboxy-, aminocarboxamidoalkyl-, cyano, alkoxyalkyl, perhaloalkyl, arylalkyloxyalkyl, and the like.

The following examples are intended to illustrate certain embodiments of the present invention, but do not exemplify the full scope of the invention.

Example 1

This example describes the synthesis of a siloxane ring-containing polymer.
Film Synthesis A silicon substrate was placed in a vacuum chamber pumped down to a base pressure of less than 10 mTorr. Trivinyltrimethylcyclotricycloxane and tert-butyl peroxide were vaporized and introduced to the chamber as gasses, along with a patch flow of argon. This gas mixture was held at a pressure of 100 mTorr using a throttle valve located downstream of the chamber. A 13.56 MHz radio frequency (RF) generator, coupled in series with matching network, was utilized at a power of 10 W to create a glow discharge between active and ground electrodes. The film was allowed to deposit on the silicon substrate, which was located on the ground electrode, to a thickness of approximately 500 nm as measured by laser interferometry. At this point, the RF generator was switched off. The vacuum chamber was then evacuated and brought to atmospheric pressure at which point the sample could be removed and examined.
FTIR Measurement The film sample was then analyzed via FTIR. An uncoated section of the same silicon wafer was first measured in a Perkin Elmer FTIR system to provide a suitable background spectrum, followed by measurement of the coated sample. All measurements were performed under inert atmosphere. The background spectrum was subtracted from the sample spectrum in order to determine the net absorbance spectrum of the coating.
Thickness Measurement A portion of the film was removed from the substrate with a razor blade, and the resultant sample was analyzed using profilometry. A Veeco Dektak 150 profilometer was used to scan the surface of the sample using a stylus. The step height as the stylus crossed from the exposed substrate to the film coating was measured, and taken to be equivalent to the film thickness.

Example 2

This example describes the synthesis of a siloxane ring-containing polymer.

The polymer films were deposited in a 0.04 $m^3$ reactor. The set-up of the reactor is similar to that described in Plasma Process. Polym. 2012, 9, 425-434. The distance between the plasma power source and the heat exchanger was 2.2 cm. The area of the plasma electrode was 1,600 $cm^2$. The monomer and initiator gases were uniformly distributed across the entire width of the substrate using a distributor tube that was 38 cm long and 0.65 cm in diameter with 15 0.5 mm holes. The monomers and initiators were used as purchased and without further purification. In this example, the monomer was trivinyltrimethylcyclotrisiloxane and the initiator was tert-butyl peroxide. The selected monomer was heated to 70° C. and fed into the chamber through a heated line at a flow rate of about 2.5 sccm. The initiator was kept at room temperature and fed into the chamber through another line at a flow rate of about 1 sccm. The substrate was formed of silicon and the size of the substrate was 7 $cm^2$. The plasma power source was held constant at the desired power (e.g., between 4 W and 130 W). The films were deposited to an average thickness of about 1000 nm as determined by profilometry.

The sample surface was examined by optical microscopy to identify the presence of defects such as delamination, pinholes or cracks. Chemical characterization of the films were performed by Fourier transform infrared (FTIR) spectroscopy. The spectrum of a bare substrate was used as the background and subtracted from the FTIR spectra. The FTIR spectra were also normalized based on the film thickness according to the following procedure:

The films were coated onto a piece of silicon wafer, then the film samples were measured in a Perkin-Elmer System 2000 FT-IR system. The absorption of a bare piece of silicon was measured as a background spectrum. The background spectrum was subtracted from the measured spectrum of each film sample to get a net FTIR absorption spectrum. Each spectrum covered a range of wavenumber from 500 $cm^{-1}$ to 4000 $cm^{-1}$.

After measurement, the spectra had baseline subtraction performed on them. Then the spectra were corrected for thickness and overlaid for comparison (see FIG. 3A). Further numerical analysis was performed on the large overlapping peaks in the 1000-1100 $cm^{-1}$ range. The individual peaks at 1000 $cm^{-1}$ and 1100 $cm^{-1}$ were deconvoluted into the individual cyclic and linear Si—O peaks, and the ratio of the peak areas was calculated.

The background subtracted and thickness-normalized FTIR spectra were analyzed to determine the percent siloxane in the polymer film according to the following formula:

$$\text{Percent cyclic siloxane in polymer} = \frac{\text{maximum absorbance of cyclic siloxane peak}}{\left(\begin{array}{c}\text{maximum absorbance of cyclic siloxane peak} + \\ \text{maximum asorbance of linear siloxane peak}\end{array}\right)} \times 100\%$$

Figure 3A:
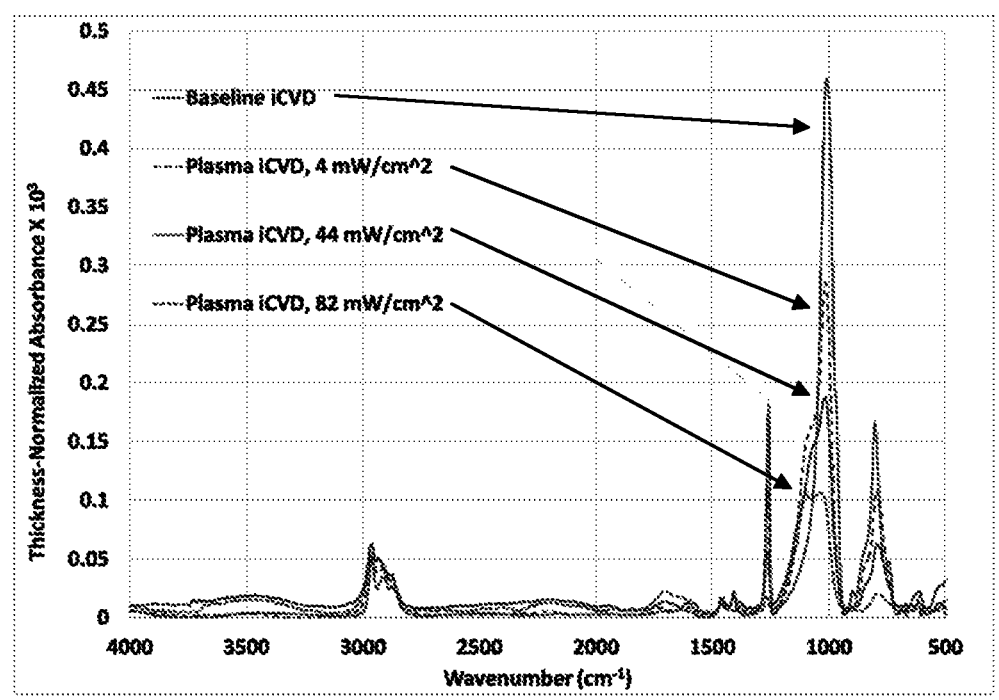
FIG. 3A shows, according to some embodiments, the Fourier Transform Infrared (FTIR) spectra of non-limiting films deposited via a variety of methods.
Figure 3B:
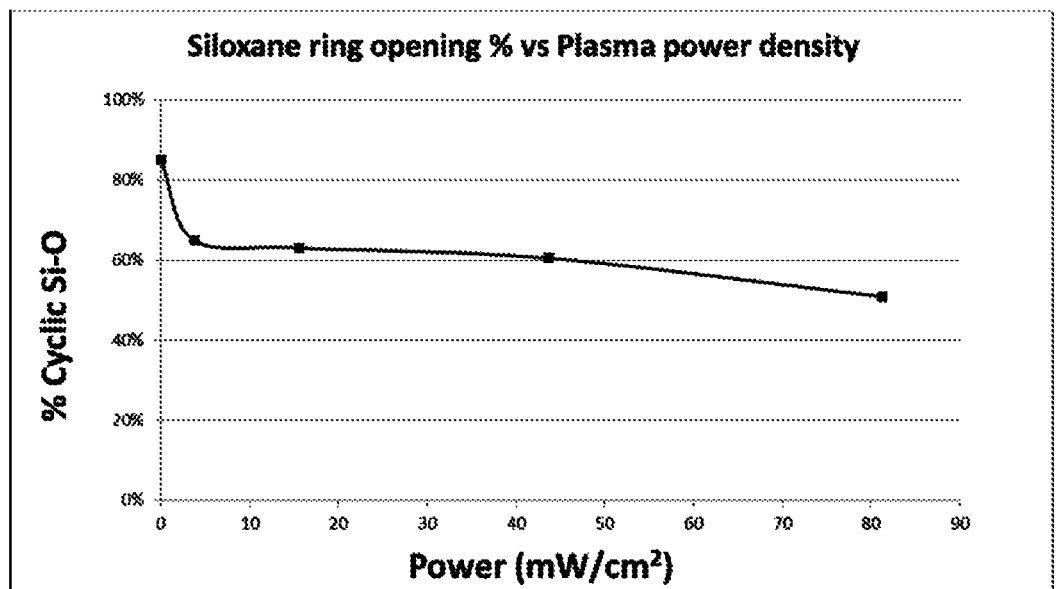
FIG. 3B shows, according to some embodiments; a chart showing the percentage of cyclic siloxane groups as a function of power density.

The maximum absorbance of the cyclic siloxane peak was the maximum absorbance observed between about 1105 cm$^{-1}$ and about 1120 cm$^{-1}$ in the FTIR spectrum. The maximum absorbance of the linear siloxane peak was the maximum absorbance between about 1070 cm$^{-1}$ and about 1105 cm$^{-1}$ in an FTIR spectrum. FIG. 3A shows exemplary background subtracted and thickness-normalized FTIR spectra from polymers synthesized using five different methods—a polymer prepared via iCVD with no plasma present, in which the majority of the cyclic siloxane groups are retained, PECVD in the presence of 6 W plasma and conditions described in this example, PECVD in the presence of 25 W plasma and conditions described in this example, PECVD in the presence of 70 W plasma and conditions described in this example and PECVD the presence of a 130 W plasma and conditions described in this example. The percent of cyclic siloxane rings for each of these polymers was determined in the manner described above. FIG. 3B shows the ratio of the maximum linear siloxane absorption peak to the maximum cyclic siloxane absorption peak for each of these five methods.

TABLE 2

| Sample Number | Plasma Power (W) | Plasma Power Density (mW/cm²) | Volumetric Plasma Power Density (mW/cm³) | Max. Absorb. Cyclic Siloxane Peak (AU) | Max. Absorb. Linear Siloxane Peak (AU) | Percent Cyclic Siloxane in Film |
|---|---|---|---|---|---|---|
| 1 | 0 | 0.0 | 0.0 | 0.414 | 0.073 | 85% |
| 2 | 6 | 3.8 | 0.2 | 0.187 | 0.101 | 65% |
| 3 | 25 | 15.6 | 0.6 | 0.329 | 0.193 | 63% |
| 4 | 70 | 43.8 | 1.8 | 0.082 | 0.054 | 60% |
| 5 | 130 | 81.3 | 3.3 | 0.031 | 0.030 | 51% |

While several embodiments of the present invention have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present invention. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described and claimed. The present invention is directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present invention.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

As used herein in the specification and in the claims, numerical ranges disclosed include, but are not limited to, ranges of volumetric plasma power densities, ranges of plasma power densities, ranges of plasma powers, ranges of temperatures, ranges of pressures, ranges of integers, ranges of force values, ranges of times, ranges of thicknesses, and ranges of gas flow rates. The disclosed ranges of any type, disclose individually each possible number that such a range could reasonably encompass, as well as any sub-ranges and combinations of sub-ranges encompassed therein. For example, disclosure of a temperature range is intended to disclose individually every possible temperature value that such a range could encompass, consistent with the disclosure herein. In another example, the disclosure of a range of volumetric plasma power densities from about 0.01 mW/cm$^3$ to about 5 mW/cm$^3$ also refers to volumetric plasma power densities that can be selected independently from about 0.01, 0.02, 0.03, 0.04, 0.05, 0.06, 0.07, 0.08, 0.09, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, and 5.0 mW/cm$^3$, as well as any range between these numbers (for example, 0.4 to 2 mW/cm$^3$), and any possible combination of ranges between these time values. Numerical ranges disclosed are inclusive of the end points of the range unless specified otherwise.

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

What is claimed is:

1. A method of fabricating a polymer via a plasma-enhanced chemical vapor deposition (PECVD) process, comprising the steps of:
    (i) flowing a precursor gas in proximity to a substrate within a reaction volume of a PECVD reactor comprising an active electrode and a ground electrode, wherein the precursor gas comprises an initiator and at least one monomer comprising a cyclic siloxane and at least two vinyl groups; and
    (ii) depositing the polymer in the presence of a plasma, wherein the deposited polymer is formed from polymerization of the at least one monomer on at least a portion of the substrate and, wherein the deposited polymer comprises one or more cyclic siloxane groups;
    wherein the initiator is present at a partial pressure of less than or equal to 10 mTorr during step (ii);
    wherein the at least one monomer is present at a partial pressure of less than or equal to 10 mTorr during step (ii);
    wherein the plasma throughout the reaction volume is substantially uniform; and
    wherein the percentage of the one or more cyclic siloxane groups in the deposited polymer in step (ii) is greater than or equal to about 60%.

2. The method of claim 1, wherein the at least one monomer comprises at least three vinyl groups.

3. The method of claim 2, wherein the at least one monomer comprises one or more of trivinyltrimethylcyclotrisiloxane, tetravinyltetramethylcyclotetrasiloxane, or trivinylpentamethyltetrasiloxane.

4. The method of claim 1, wherein the percentage of the cyclic siloxane groups in the polymer is greater than or equal to about 65%.

5. The method of claim 1, wherein the deposited polymer is a film that has a thickness of greater than or equal to 50 nm and less than or equal to 10 μm.

6. The method of claim 1, wherein the deposited polymer is a film that has a dielectric constant of less than or equal to 3.

7. The method of claim 1, wherein the initiator comprises a peroxide.

8. The method of claim 7, wherein the peroxide is tert-butyl peroxide or is tert-amyl peroxide.

9. The method of claim 1, wherein the substrate comprises one or more of gold, copper, solder, solder flux, indium phosphide, gallium sulfide, gallium nitride, and silicon.

10. The method of claim 1, wherein the active electrode is located at a distance to the ground electrode wherein the distance is greater than or equal to 1 cm.

11. The method of claim 1, wherein the plasma uniformity exhibits a ratio of the standard deviation of a power density of the plasma over the reaction volume of less than or equal to 25%.

12. The method of claim 1, wherein the ratio of the partial pressure of the initiator to the partial pressure of the at least one monomer is less than or equal to 2 during step (ii).

13. The method of claim 1, wherein the partial pressures of the initiator and the at least one monomer are each independently less than or equal to 10 mTorr during step (ii).

14. The method of claim 1, wherein the total pressure of the PECVD reactor is less than or equal to 75 mTorr during step (ii).

15. The method of claim 1, wherein the deposited polymer exhibits no fungal growth, as measured by ASTM G-21.

16. The method of claim 1, wherein the deposited polymer has an insulation resistance of greater than or equal to $1.5*10^{12}$ ohms and less than or equal to $10^{14}$ ohms.

17. The method of claim 1, wherein the deposited polymer exhibits a dielectric breakdown voltage of greater than or equal to 5,000 V/mil.

18. The method of claim 1, wherein the adhesion strength of the deposited polymer after undergoing elongation of up to 5% is greater than or equal to 75% of the initial adhesion strength.

19. The method of claim 1, wherein the deposited polymer on at least a portion of the substrate reduces or prevents corrosion of the substrate, as compared to the substrate prior to depositing the polymer thereon, as measured using a salt fog test, conducted in accordance with Method 509.5 5 in MIL-STD-810G.

* * * * *